(12) United States Patent
Cheng et al.

(10) Patent No.: US 8,338,455 B2
(45) Date of Patent: Dec. 25, 2012

(54) COMPOUNDS AND METHODS OF USE

(75) Inventors: Yuan Cheng, Newbury Park, CA (US); Deborah Choquette, Medford, MA (US); Jean-Christophe Harmange, Andover, MA (US); Andrew Tasker, Simi Valley, CA (US)

(73) Assignee: Amgen Inc., Thousand Oaks, CA (US)

( * ) Notice: Subject to any disclaimer, the term of this patent is extended or adjusted under 35 U.S.C. 154(b) by 953 days.

(21) Appl. No.: 12/004,156

(22) Filed: Dec. 19, 2007

(65) Prior Publication Data

US 2008/0161346 A1 Jul. 3, 2008

Related U.S. Application Data

(60) Provisional application No. 60/876,283, filed on Dec. 20, 2006.

(51) Int. Cl.
*C07D 401/02* (2006.01)
*A61K 31/47* (2006.01)
(52) U.S. Cl. ......... 514/308; 514/307; 546/140; 546/144
(58) Field of Classification Search ........................ None
See application file for complete search history.

(56) References Cited

U.S. PATENT DOCUMENTS

| 6,372,736 | B1 | 4/2002 | Kemp et al. | |
|---|---|---|---|---|
| 2004/0034028 | A1* | 2/2004 | Guevel et al. | 514/249 |

FOREIGN PATENT DOCUMENTS

| EP | 0416581 A1 | 3/1991 |
|---|---|---|
| WO | WO 01/17995 A1 | 3/2001 |
| WO | WO 2005/070891 A2 | 8/2005 |
| WO | WO 2005/073224 A2 | 8/2005 |
| WO | WO 2006/116713 A1 | 4/2006 |

OTHER PUBLICATIONS

Carato et al., "Synthesis and in vitro binding studies of substituted piperdine naphthamides. Part II: Influence of the substitution on the benzyl moiety on the affinity for D2L, D4.2, and 5-HT2A receptors," Bioorganic & Medicinal Chemistry, 17 (6), 1570-1574 (2007).

* cited by examiner

*Primary Examiner* — Zinna Northington Davis
(74) *Attorney, Agent, or Firm* — Joseph W. Bulock

(57) ABSTRACT

Selected compounds are effective for prophylaxis and treatment of diseases, such as VEGF mediated diseases. The invention encompasses novel compounds, analogs, prodrugs and pharmaceutically acceptable salts thereof, pharmaceutical compositions and methods for prophylaxis and treatment of diseases and other maladies or conditions involving, cancer and the like. The subject invention also relates to processes for making such compounds as well as to intermediates useful in such processes.

17 Claims, No Drawings

COMPOUNDS AND METHODS OF USE

This application claims priority to U.S. Provisional Application Ser. No. 60/876,283 filed Dec. 20, 2006 the entirety of which is incorporated herein by reference.

FIELD OF THE INVENTION

This invention is in the field of pharmaceutical agents and specifically relates to compounds, compositions, uses and methods for treating inflammation, angiogenesis and cancer.

BACKGROUND OF THE INVENTION

Protein kinases represent a large family of proteins which play a central role in the regulation of a wide variety of cellular processes, maintaining control over cellular function. A partial list of such kinases includes abl, Akt, bcr-abl, Blk, Brk, Btk, c-kit, c-Met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Inhibition of such kinases has become an important therapeutic target.

Certain diseases are known to be associated with deregulated angiogenesis, for example ocular neovascularisation, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias).

At the center of the network regulating the growth and differentiation of the vascular system and its components, both during embryonic development and normal growth, and in a wide number of pathological anomalies and diseases, lies the angiogenic factor known as Vascular Endothelial Growth Factor" (VEGF; originally termed "Vascular Permeability Factor", VPF), along with its cellular receptors (see G. Breier et al., Trends in Cell Biology, 6:454-456 (1996)).

VEGF is a dimeric, disulfide-linked 46-kDa glycoprotein related to "Platelet-Derived Growth Factor" (PDGF); it is produced by normal cell lines and tumor cell lines; is an endothelial cell-specific mitogen; shows angiogenic activity in in vivo test systems (e.g. rabbit cornea); is chemotactic for endothelial cells and monocytes; and induces plasminogen activators in endothelial cells, which are involved in the proteolytic degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placenta Growth Factor" (P1GF) and VEGF-C.

VEGF receptors (VEGFR) are transmembranous receptor tyrosine kinases. They are characterized by an extracellular domain with seven immunoglobulin-like domains and an intracellular tyrosine kinase domain. Various types of VEGF receptor are known, e.g. VEGFR-1 (also known as flt-1), VEGFR-2 (also known as KDR), and VEGFR-3.

A large number of human tumors, especially gliomas and carcinomas, express high levels of VEGF and its receptors. This has led to the hypothesis that the VEGF released by tumor cells stimulates the growth of blood capillaries and the proliferation of tumor endothelium in a paracrine manner and through the improved blood supply, accelerate tumor growth. Increased VEGF expression could explain the occurrence of cerebral edema in patients with glioma. Direct evidence of the role of VEGF as a tumor angiogenesis factor in vivo is shown in studies in which VEGF expression or VEGF activity was inhibited. This was achieved with anti-VEGF antibodies, with dominant-negative VEGFR-2 mutants which inhibited signal transduction, and with antisense-VEGF RNA techniques. All approaches led to a reduction in the growth of glioma cell lines or other tumor cell lines in vivo as a result of inhibited tumor angiogenesis.

Angiogenesis is regarded as an absolute prerequisite for tumors which grow beyond a diameter of about 1-2 mm; up to this limit, oxygen and nutrients may be supplied to the tumor cells by diffusion. Every tumor, regardless of its origin and its cause, is thus dependent on angiogenesis for its growth after it has reached a certain size.

Three principal mechanisms play an important part in the activity of angiogenesis inhibitors against tumors: 1) Inhibition of the growth of vessels, especially capillaries, into avascular resting tumors, with the result that there is no net tumor growth owing to the balance that is achieved between cell death and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels. See R. Connell and J. Beebe, Exp. Opin. Ther. Patents, 11:77-114 (2001).

VEGFs are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production.

Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF-mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features. As such, regulators of angiogenesis have become an important therapeutic target.

Recent work on the relationship between inhibition of angiogenesis and the suppression or reversion of tumor progression shows great promise in the treatment of cancer (Nature, 390:404-407 (1997)), especially the use of multiple angiogenesis inhibitors compared to the effect of a single inhibitor. Angiogenesis can be stimulated by HGF, as well as vascular endothelial growth factor (VEGF) and basic fibroblast growth factor (bFGF).

Angiogenesis, the process of sprouting new blood vessels from existing vasculature and arteriogenesis, the remodeling of small vessels into larger conduit vessels are both physiologically important aspects of vascular growth in adult tissues. These processes of vascular growth are required for beneficial processes such as tissue repair, wound healing, recovery from tissue ischemia and menstrual cycling. They are also required for the development of pathological conditions such as the growth of neoplasias, diabetic retinopathy, rheumatoid arthritis, psoriasis, certain forms of macular degeneration, and certain inflammatory pathologies. The inhibition of vascular growth in these contexts has also shown beneficial effects in preclinical animal models. For example, inhibition of angiogenesis by blocking vascular endothelial growth factor or its receptor has resulted in inhibition of tumor growth and in retinopathy. Also, the development of pathological pannus tissue in rheumatoid arthritis involves angiogenesis and might be blocked by inhibitors of angiogenesis.

The ability to stimulate vascular growth has potential utility for treatment of ischemia-induced pathologies such as myocardial infarction, coronary artery disease, peripheral vascular disease, and stroke. The sprouting of new vessels and/or the expansion of small vessels in ischemic tissues prevents ischemic tissue death and induces tissue repair. Certain diseases are known to be associated with deregulated angiogenesis, for example ocular neovascularization, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias).

T cells play a pivotal role in the regulation of immune responses and are important for establishing immunity to pathogens. In addition, T cells are often activated during inflammatory autoimmune diseases, such as rheumatoid arthritis, inflammatory bowel disease, type I diabetes, multiple sclerosis, Sjogren's disease, myasthenia gravis, psoriasis, and lupus. T cell activation is also an important component of transplant rejection, allergic reactions, and asthma.

T cells are activated by specific antigens through the T cell receptor (TCR) which is expressed on the cell surface. This activation triggers a series of intracellular signaling cascades mediated by enzymes expressed within the cell (Kane, L P et al. Current Opinion in Immunol. 200, 12, 242). These cascades lead to gene regulation events that result in the production of cytokines, like interleukin-2 (IL-2). IL-2 is a critical cytokine in T cell activation, leading to proliferation and amplification of specific immune responses.

One class of enzymes shown to be important in signal transduction is the kinase enzymes Members of the Src-family of tyrosine kinases include, for example: Lck, Fyn(B), Fyn(T), Lyn, Src, Yes, Hck, Fgr and Blk (for review see: Bolen, J B, and Brugge, J S Annu. Rev. Immunol 1997, 15, 371). Gene disruption studies suggest that inhibition of some members of the src family of kinases would potentially lead to therapeutic benefit. Src(-/-) mice have abnormalities in bone remodeling or osteopetrosis (Soriano, P. Cell 1991, 64, 693), suggesting that inhibition of this kinase might be useful in diseases of bone resorption, such as osteoporosis. Lck(-/-) mice have defects in T cell maturation and activation (Anderson, S J et al. Adv. Immunol. 1994, 56, 151), suggesting that inhibition of this kinase might be useful in diseases of T cell mediated inflammation. In addition, human patients have been identified with mutations effecting Lck kinase activity (Goldman, F D et al. J. Clin. Invest. 1998, 102, 421). These patients suffer from a severe combined immunodeficiency disorder (SCID).

Without wishing to imply that the compounds disclosed in the present invention possess pharmacological activity only by virtue of an effect on a single biological process, it is believed that the compounds modulate T cell activation by way of inhibition of one or more of the multiple protein tyrosine kinases involved in early signal transduction steps leading to T cell activation, for example by way of inhibition of Lck kinase.

Src-family kinases are also important for signaling downstream of other immune cell receptors. Fyn, like Lck, is involved in TCR signaling in T cells (Appleby, M W et al. Cell 1992, 70, 751). Hck and Fgr are involved in Fcγ receptor signaling leading to neutrophil activation (Vicentini, L. et al. J. Immunol. 2002, 168, 6446). Lyn and Src also participate in Fcγ receptor signaling leading to release of histamine and other allergic mediators (Turner, H. and Kinet, J-P Nature 1999, 402, B24). These findings suggest that Src family kinase inhibitors may be useful in treating allergic diseases and asthma.

PCT publication WO 03/000660 describes substituted phenyl compounds. Substituted quinolines are described in U.S. Pat. No. 6,143,764. WO 02/32872 describes substituted quinolines. WO 00/47212 describes substituted quinazoline derivatives.

Compounds of the current invention have not been described for the treatment of cancer and inflammation.

DESCRIPTION OF THE INVENTION

A class of compounds useful in treating cancer and angiogenesis is defined by Formula I

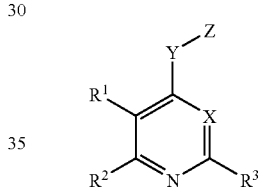

enantiomers, diastereomers, salts and solvates thereof wherein
X is $CR^1$ or N; and
Y is $(C_1-C_6)$alkylene, or $(C_1-C_6)$alkenylene wherein substituents on the same carbon atom or on adjacent carbon atoms may optionally combine to form a $C_3$ to $C_6$-membered cycloalkyl ring, or a $C_5-C_6$ heterocyclyl ring.
Z is

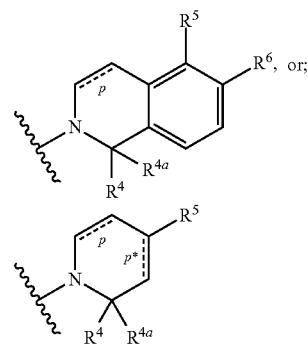

p and p* are each independently absent or a bond;
$R^1$ at each occurrence is independently
  a) H, halo, or
  b) alkyl, cycloalkyl, alkenyl, alkynyl, aryl, heteroaryl, heterocyclo, arylalkyl, heteroarylalkyl, cycloalkylalkyl, or heterocycloalkyl, any of which may be optionally independently substituted with one or more $R^{10}$;

$R^2$ is H, $NR^7$, $NHC(=O)NR^8R^9$, $NHC(=S)NR^8R^9$, or $R^1$ and $R^2$ together with the ring to which they are bonded combine to form a ring selected from quinoline, quinazoline, azaindole, pyrrolo[2,3-d]pyrimidine, azabenzothiophene, thieno[3,2-b]pyridine, naphthyridine, and azaindazole, any of which may be optionally independently substituted with one or more $R^{10}$;

$R^3$ is H, $NHR^7$, $C(=O)NHR^7$, $NHC(=O)NR^8R^9$, $NHC(=S)NR^8R^9$;

$R^4$ and $R^{4a}$ are independently selected from H, and alkyl, or $R^4$ and $R^{4a}$ combine to form =O $R^5$ is H, $C(=O)NHR^7$, $NHC(=O)NHR^7$ or $NHC(=O)R^7$;

$R^6$ is H, halo, $C(=O)NHR^7$ or $NHC(=O)R^7$, $NHC(=O)NR^8R^9$;

$R^7$ is independently at each occurrence
  a) H, or
  b) alkyl, cycloalkyl, heterocyclo, aryl, heteroaryl, cycloalkyl, alkyl, arylalkyl, alkoxyalkyl, heteroarylalkyl, cycloalklyalkyl, and 2,3-dihydroindole any of which can be optionally substituted with one or more $R^{10}$;

$R^{10}$ is halo, alkyl, alkenyl, alkynyl, alkoxy, haloalkyl, cycloalkyl, heterocyclo, aryl, heteroaryl, arylalkyl, heteroarylalkyl, cycloalkylalkyl, heterocycloalkyl, cyano, nitro, $-NR^8R^9$ or $-C(=O)NR^8R^9$, $NHC(=O)NR^8R^9$;

$R^8$ and $R^9$ are independently H, alkyl, haloalkyl, cycloalkyl, heterocyclo, aryl, heteroaryl, arylalkyl, heteroarylalkyl, cycloalkylalkyl, and heterocycloalkyl any of which may be optionally independently substituted with one or more $R^{10}$.

Preferred compounds of formula I include compounds where Z is

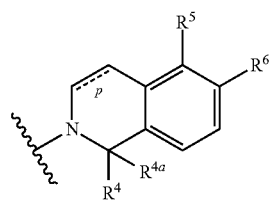

and p is absent.

Preferred compounds of formula I include compounds where Z is

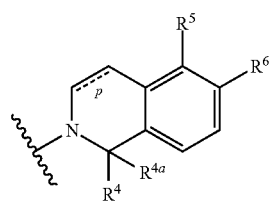

and p is a bond.

Preferred compounds of formula I include compounds where Z is

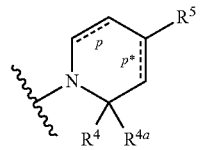

and p and p* are each absent

Preferred compounds of formula I include compounds where Y is methylene.

Preferred compounds of formula I include compounds where Y is ethenylene.

Preferred compounds of formula I include compounds where $R^1$ and $R^2$ are each hydrogen; or combine to form a ring selected from 6,7-dimethoxyquinoline, and quinoline.

Preferred compounds of formula I include compounds wherein Y is $CH_2$; and
$R^5$ is $C(=O)NHR^7$, or $NHC(=O)R^8$.

Preferred compounds of formula I include compounds wherein Y is $CH_2$; $R^5$ is $C(=O)NHR^7$, or $NHC(=O)R^8$, and $R^7$ and $R^8$ are independently phenyl, cycloalkyl or 2,3-dihydroindole any of which may be optionally independently substituted with one or more $R^{10}$.

Preferred compounds of the invention include compounds of the following formula II

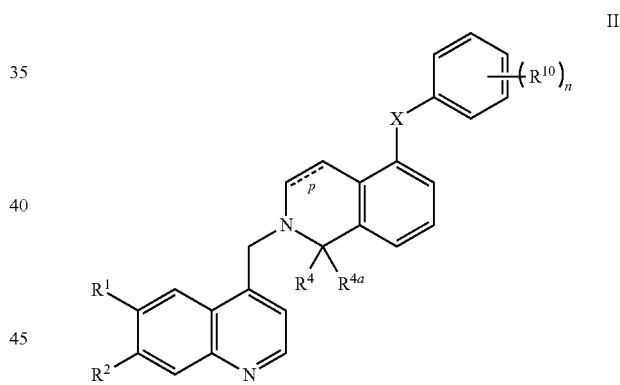

enantiomers, diastereomers, salts and solvates thereof wherein $R^1$ and $R^2$ are independently H or alkoxy;

$R^4$ and $R^{4a}$ are each hydrogen, or $R^4$ and $R^4$ combine to form =O;

p is absent or a bond;

X is $-C(=O)NH-$, $-NHC(=O)NH-$ or $-NHC(=O)-$, $R^{10}$ is independently selected at each occurrence from halo, alkyl, alkenyl, alkynyl, alkoxy, haloalkyl, cycloalkyl, heterocyclo, aryl, heteroaryl, arylalkyl, heteroarylalkyl, cycloalkylalkyl, heterocycloalkyl, cyano, nitro, $-NR^8R^9$ or $-C(=O)NR^8R^9$, $R^8$ and $R^9$ are independently H, alkyl, haloalkyl, cycloalkyl, heterocyclo, aryl, heteroaryl, arylalkyl, heteroarylalkyl, cycloalkylalkyl, and heterocycloalkyl any of which may be optionally independently substituted with one or more $R^{10}$.

n is 0, 1, 2 or 3.

Preferred compounds of the invention further include compounds of the following formula III:

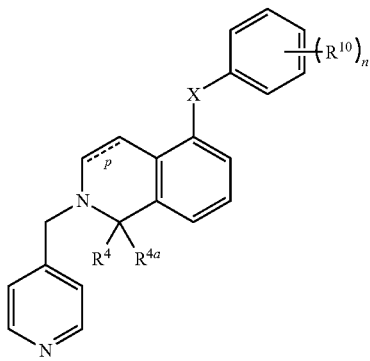

enantiomers, diastereomers, salts and solvates thereof wherein
$R^4$ and $R^{4a}$ are each hydrogen, or $R^4$ and $R^4$ combine to form =O
p is absent or a bond;
X is —C(=O)NIH—, —NHC(=O)NH— or —NHC(=O)—,
$R^{10}$ is independently selected at each occurrence from halo, alkyl, alkenyl, alkynyl, alkoxy, haloalkyl, cycloalkyl, heterocyclo, aryl, heteroaryl, arylalkyl, heteroarylalkyl, cycloalkylalkyl, heterocycloalkyl, cyano, nitro, —$NR^8R^9$ or —C(=O)$NR^8R^9$,
$R^8$ and $R^9$ are independently H, alkyl, haloalkyl, cycloalkyl, heterocyclo, aryl, heteroaryl, arylalkyl, heteroarylalkyl, cycloalkylalkyl, and heterocycloalkyl any of which may be optionally independently substituted with one or more $R^{10}$; and
n is 0, 1, 2 or 3.

Preferred compounds of the invention include compounds of the following formula IV

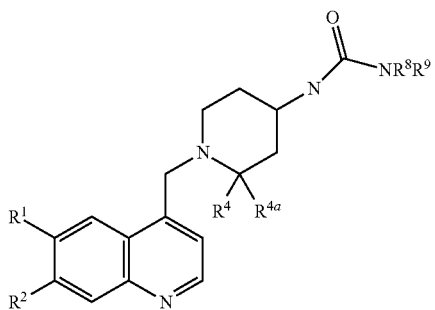

enantiomers, diastereomers, salts and solvates thereof wherein
$R^1$ and $R^2$ are independently H or alkoxy;
$R^4$ and $R^{4a}$ are each hydrogen, or $R^4$ and $R^4$ combine to form =O; and
$R^8$ and $R^9$ are independently H, alkyl, haloalkyl, cycloalkyl, heterocyclo, aryl, heteroaryl, arylalkyl, heteroarylalkyl, cycloalkylalkyl, and heterocycloalkyl any of which may be optionally independently substituted with one or more $R^{10}$, any of which may be optionally independently substituted with one or more $R^{10}$.

The invention further relates to pharmaceutical compositions continuing the above compounds.

The invention further relates to a method of treating cancer in a subject, said method comprising administering an effective amount of a compound shown above.

The invention further relates to a method of treating angiogenesis in a subject, said method comprising administering an effective amount of a compound shown above.

The invention further relates to a method of treating proliferation-related disorders in a mammal, said method comprising administering an effective amount of a compound shown abouve.

The invention further relates to a method of reducing blood flow in a tumor in a subject, said method comprising administering an effective amount of a compound shown above.

The invention further relates to a method of reducing blood flow in a tumor in a subject, said method comprising administering an effective amount of a compound shown above.

The invention further relates to a method of reducing tumor size in a subject, said method comprising administering an effective amount of a compound shown above.

The invention further relates to a method of treating diabetic retinopathy in a subject, said method comprising administering an effective amount of a compound shown above.

The invention further relates to a method of treating inflammation in a mammal, the method comprising administering to the mammal a therapeutically effective amount of a compound shown above.

The invention further relates to a method of inhibiting T cell activation in a mammal, the method comprising administering to the mammal a therapeutically effective amount of a compound shown above.

The invention further relates to a method of treating arthritis, rheumatoid arthritis, psoriatic arthritis, or osteoarthritis in a mammal, the method comprising administering to the mammal a therapeutically effective amount of a compound shown above.

The invention further relates to a method of treating organ transplant, acute transplant or heterograft or homograft rejection, or transplantation tolerance induction in a mammal, the method comprising administering to the mammal a therapeutically effective amount of a compound shown above.

The invention further relates to a method of treating ischemic or reperfusion injury, myocardial infarction, or stroke in a mammal, the method comprising administering to the mammal a therapeutically effective amount of a compound shown above.

The invention further relates to a method of treating multiple sclerosis, inflammatory bowel disease, including ulcerative colitis, Crohn's disease, lupus, contact hypersensitivity, delayed-type hypersensitivity, and gluten-sensitive enteropathy, type 1 diabetes, psoriasis, contact dermatitis, Hashimoto's thyroiditis, Sjogren's syndrome, autoimmune hyperthyroidism, Addison's disease, autoimmune polyglandular disease, autoimmune alopecia, pernicious anemia, vitiligo, autoimmune hypopituitarism, Guillain-Barre syndrome, glomerulonephritis, serum sickness, uticaria, allergic diseases, asthma, hayfever, allergic rhinitis, scleracielma, mycosis fungoides, dermatomyositis, alopecia greata, chronic actinic dermatitis, eczema, Behcet's disease, Pustulosis palmoplanteris, Pyoderma gangrenum, Sezary's syndrome, atopic dermatitis, systemic schlerosis, morphea or atopic dermatitis in a mammal, the method comprising administering to the mammal a therapeutically-effective amount of a compound shown above.

Indications

Compounds of the present invention would be useful for, but not limited to, the prevention or treatment of angiogenesis related diseases. The compounds of the invention have kinase inhibitory activity, such as VEGFR/KDR, c-kit, and abl. The compounds of the invention are useful in therapy as antineoplasia agents or to minimize deleterious effects of VEGF. The compounds of the invention also inhibit lck and src activity.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Preferably, the compounds are useful for the treatment of neoplasia selected from lung cancer, colon cancer and breast cancer.

The compounds also would be useful for treatment of opthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are useful in therapy of proliferative diseases. These compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermato-myositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof. An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further especially applicable to the treatment of inflammation, e.g. inflammatory disease or condition, of connective tissues including dermatomyositis and myositis.

These compounds can be used as active agents against such disease states as arthritis, atherosclerosis, psoriasis, hemangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

The compounds of the present invention are also useful in the treatment of ulcers including bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of sub-cutaneous fat and for the treatment of obesity.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the present invention are also useful in the treatment of cardiovascular conditions such as atherosclerosis, restenosis, arteriosclerosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention are also useful in the treatment of diabetic conditions such as diabetic retinopathy and microangiopathy.

Accordingly, the invention relates to a method of treating inflammation in a mammal, the method comprising administering to the mammal a therapeutically effective amount of a compound according to any one of the above embodiments.

The invention relates to a method of inhibiting T cell activation in a mammal, the method comprising administering to the mammal a therapeutically effective amount of a compound according to any one of the above embodiments.

The invention relates to a method of treating arthritis, rheumatoid arthritis, psoriatic arthritis, or osteoarthritis in a mammal, the method comprising administering to the mammal a therapeutically effective amount of a compound according to any one of the above embodiments.

The invention relates to a method of treating organ transplant, acute transplant or heterograft or homograft rejection, or transplantation tolerance induction in a mammal, the method comprising administering to the mammal a therapeutically effective amount of a compound according to any one of the above embodiments.

The invention relates to a method of treating ischemic or reperfusion injury, myocardial infarction, or stroke in a mammal, the method comprising administering to the mammal a therapeutically effective amount of a compound according to any one of the above embodiments.

The compounds of this invention may also act as inhibitors of other protein kinases, e.g. tie-2, lck, src, fgf, ron, and ret, and thus be effective in the treatment of diseases associated with other protein kinases. The compounds of this invention may also act as inhibitors of mutants of the above-identified tyrosine kinases, including c-kit, abl and VEGFR.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Where the plural form is used for compounds, salts, and the like, this is taken to mean also a single compound, salt and the like.

DEFINITIONS

"Angiogenesis" is defined as any alteration of an existing vascular bed or the formation of new vasculature which benefits tissue perfusion. This includes the formation of new vessels by sprouting of endothelial cells from existing blood vessels or the remodeling of existing vessels to alter size, maturity, direction or flow properties to improve blood perfusion of tissue.

The terms "treating," "treatment," and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

The term "treatment" includes therapeutic treatment as well as prophylactic treatment (either preventing the onset of disorders altogether or delaying the onset of a pre-clinically evident stage of disorders in individuals).

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to inhibit angiogenesis.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" (or "alkylene") embraces bridging divalent alkyl radicals such as methylenyl (methylene) and ethylenyl (ethylene). The term "lower alkyl substituted with $R^2$" does not include an acetal moiety.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations. The term "alkenylene" embraces bridging divalent alkylene radicals.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, amino, alkoxy and lower alkylamino. Phenyl substituted with —O—CH$_2$—O— forms the aryl benzodioxolyl substituent.

The term "heterocyclyl" embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3, 4-thiadiazolyl, 1,2,5-thiadiazolyl].

The term heterocyclyl also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heterocyclyl include pyranyl, 2-furyl, 3-furyl, 2-thienyl, 3-thienyl, benzofuryl, benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydrobenzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "aminocarbonyl" denotes an amide group of the formula —C(=O)NH$_2$.

The terms "N-alkylaminocarbonyl" and "N,N-dialkylaminocarbonyl" denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The terms "heterocyclylalkylenyl" and "heterocyclylalkyl" embrace heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical.

Even more preferred are lower heteroarylalkylenyl radicals having alkyl portions of one to three carbon atoms. Examples include such radicals as pyridylmethyl and thienylmethyl.

The term "aralkyl" (or "arylalkyl") embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylamino" embraces "N-alkylamino" and "N,N-dialkylamino" where amino groups are independently substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups which have been substituted with one or two aryl radicals, such as N-phenylamino. The arylamino radicals may be further substituted on the aryl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "aralkylamino" denotes amino groups which have been substituted with one or two aralkyl radicals. More preferred are phenyl-$C_1$-$C_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups which have been independently substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminomethoxyethoxy, N-methylaminoethoxyethoxy, N,N-dimethylaminoethoxyethoxy, N,N-diethylaminomethoxymethoxy and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, carboxypropyl, and the like. Even more preferred are lower carboxyalkyl radicals having one to three $CH_2$ groups.

The term "aryloxy" embraces optionally substituted aryl radicals, as defined above, attached to an oxygen atom. Examples of such radicals include phenoxy.

The term "arylalkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Even more preferred are "5-6-membered cycloalkylalkyl" attached to alkyl portions having one to three carbon atoms. Examples of such radicals include cyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Preferred cycloalkenyl groups include $C_3$-$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The term "Formulas I-IV" includes any sub formulas.

The compounds of the invention are endowed with kinase inhibitory activity, such as Lck, KDR and/or c-Met inhibitory activity.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of Lck, KDR and/or c-Met.

The present invention comprises a pharmaceutical composition comprising a therapeutically-effective amount of a compound of Formulas I-IV in association with a least one pharmaceutically-acceptable carrier, adjuvant or diluent.

The present invention also comprises a method of treating angiogenesis related disorders in a subject having or susceptible to such disorder, the method comprising treating the subject with a therapeutically-effective amount of a compound of Formula I-IV.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Teclmology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with other agents, such as other kinase inhibitors including p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors, and anti-inflammatories.

The present invention comprises processes for the preparation of a compound of Formula I-IV.

Also included in the family of compounds of Formula I-IV are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I-IV may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formula I-IV include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formula I-IV. When a basic group and an acid group are present in the same molecule, a compound of Formula I-IV may also form internal salts.

General Synthetic Procedures

The compounds of the invention can be synthesized according to the following procedures of Schemes 1-11, wherein the substituents are as defined for Formulas I-IV, above, except where further noted.

The following abbreviations are used throughout the specification:

| | |
|---|---|
| AcOH | acetic acid |
| BINAP | 2,2'-bis(diphenylphosphino)-1,1'-binapthyl |
| BBr$_3$ | boron tribromide |
| BH$_3$-THF | borane-tetrahydrofuran complex |
| BOC | t-butoxycarbonyl |
| BSA | bovine serum albumin |
| n-BuLi | n-butyl lithium |
| CO | carbon monoxide |
| C$_2$O$_2$Cl$_2$ or (COCl)$_2$ | oxalyl chloride |
| Cs$_2$CO$_3$ | cesium carbonate |
| CHCl$_3$ | chloroform |
| Et$_2$O | diethyl ether |
| DCM, CH$_2$Cl$_2$ | methylene chloride |
| DIBAL | diisobutylaluminum hydride |
| DIEA, DIPEA, Hunig's base | diisopropylethylamine |
| DMF | dimethylformamide |
| dppa | diphenylphosphoryl azide |
| DPPP | 1,3-diphenylphosphino propane |
| DMAP | 4-dimethylaminopyridine |
| EtOAc, EA | ethyl acetate |
| EtOH | ethanol |
| Et$_2$O | diethyl ether |
| EDC, EDCI | 1-(3-dimethylaminopropyl)-3-ethylcarbodiimide hydrochloride |
| EtNH$_2$ | ethyl amine |
| FBS | fetal bovine serum |
| g | gram |
| h | hour |
| HCl | hydrochloric acid |
| HOAt | 1-hydroxy-7-azabenzotriazole |
| HOBt | 1-hydroxybenzotriazole hydrate |
| H$_2$ | hydrogen |
| H$_2$0 | water |
| H$_2$O$_2$ | hydrogen peroxide |
| HATU | O-(7-azabenzotriazol-1-yl-)N,N,N',N', tetramethyluronium hexafluorophosphate |
| KOH | potassium hydroxide |
| K$_2$CO$_3$ | potassium carbonate |
| K$_3$PO$_4$ | potassium phosphate |
| KMnO$_4$ | potassium permanganate |
| LAH | lithium aluminum hydride |
| LiHMDS | lithium bis(trimethylsilyl)-amide |
| LiOH | lithium hydroxide |
| MgSO$_4$ | magnesium sulfate |
| MCPBA | meta-chloroperbenzoic acid |
| MeOH, CH$_3$OH | methanol |
| MeNH$_2$ | methyl amine |
| NH$_4$Cl | ammonium chloride |
| NH$_4$OH | ammonium hydroxide |
| NMP | N-methylpyrrolidinone |
| NaHCO$_3$ | sodium bicarbonate |
| NaN$_3$ | sodium azide |
| Na$_2$SO | sodium sulfate |
| NaOH | sodium hydroxide |
| NaH | sodium hydride |
| Na$_2$SO$_4$ | sodium sulfate |
| NaOt-Bu | sodium tert-butoxide |
| NaHB(OAc)$_3$ | sodium triacetoxyborohydride |
| N$_2$ | nitrogen |
| O/N | overnight |
| POCl$_3$ | phosphorus oxychloride |
| Pd/C | palladium on carbon |

| | |
|---|---|
| Pd₂(dba)₃ | bis(dibenzylideneacetone) palladium |
| Pd(OAC)₂ | palladium (II) acetate |
| P(t-bu)₃ | tri(tert-butyl)phosphine |
| PBS | phospate buffered saline |
| PyBop | Benzotriazol-1-yl-oxy-tripyrrolidino-phosphonium hexafluorophosphate |
| RT | room temperature |
| SOCl₂ | thionyl chloride |
| TBTU | O-benzotriazol-1-yl-N,N,N',N'-tetramethyluronium tetrafluoroborate |
| TBAI | tetrabutylammonium iodide |
| TFA | trifluoroacetic acid |
| THF | tetrahydrofuran |
| TEA, Et₃N | triethylamine |

The starting compounds defined in the Schemes may also be present with functional groups in protected form if necessary and/or in the form of salts, provided a salt-forming group is present and the reaction in salt form is possible. If so desired, one compound of Formula I can be converted into another compound of Formula I, e.g. an N-oxide thereof; a compound of Formula I can be converted into a salt; a salt of a compound of Formula I can be converted into the free compound or another salt; and/or a mixture of isomeric compounds of Formula I can be separated into the individual isomers.

N-Oxides can be obtained in a known matter by reacting a compound of Formula I with hydrogen peroxide, oxone, or a peracid, e.g. mCPBA, in an inert solvent, e.g. $CH_2Cl_2$, or a mixture of water and an alcohol such as MeOH or EtOH, at a temperature between about −10-35° C., such as about 0° C.-RT.

If one or more other functional groups, for example carboxy, hydroxy, amino, or mercapto, are or need to be protected in a compound of Formula I or in the preparation of compounds of Formula I, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York (1973), in T. W. Greene, "Protective Groups in Organic Synthesis", Wiley, New York (1981), in "The Peptides", Volume 3, E. Gross and J. Meienhofer editors, Academic Press, London and New York (1981), in "Methoden der organischen Chemie" (Methods of Organic Chemistry), Houben Weyl, 4$^{th}$ edition, Volume 15/1, Georg Thieme Verlag, Stuttgart (1974), in H.-D. Jakubke and H. Jescheit, "Aminosäuren, Peptide, Proteine" (Amino Acids, Peptides, Proteins), Verlag Chemie, Weinheim, Deerfield Beach, and Basel (1982), and in Jochen Lehmann, "Chemie der Kohlenhydrate: Monosaccharide und Derivate" (Chemistry of carbohydrates: monosaccharides and derivatives), Georg Thieme Verlag, Stuttgart (1974).

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of Formula I with a salt-forming group may be prepared in a manner known per se. Acid addition salts of compounds of Formula I may thus be obtained by treatment with an acid or with a suitable anion exchange reagent. A salt with two acid molecules (for example a dihalogenide of a compound of Formula I) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of Formula I.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H⁺ form, depending on the type of reaction and/or reactants at reduced, normal, or elevated temperature, for example in the range from about −100° C. to about 190° C., preferably from about −80° C. to about 150° C., for example at about −80 to about 60° C., at room temperature, at about −20 to about 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include for example water, esters, typically lower alkyl-lower alkanoates, e.g., EtOAc, ethers, typically aliphatic ethers, e.g., $Et_2O$, or cyclic ethers, e.g., THF, liquid aromatic hydrocarbons, typically benzene or toluene, alcohols, typically MeOH, EtOH or 1-propanol, IPOH, nitriles, typically $CH_3CN$, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g., AcOH, carboxylic acid anhydrides, typically lower alkane acid anhydrides, e.g., acetic anhydride, cyclic, linear, or branched hydrocarbons, typically cyclohexane, hexane, or isopentane, or mixtures of these solvents, e.g., aqueous solutions, unless otherwise stated in the description of the process. Such solvent mixtures may also be used in processing, for example in chromatography.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of Formula I, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds of this invention may also be represented in multiple tautomeric forms, for example, as illustrated below:

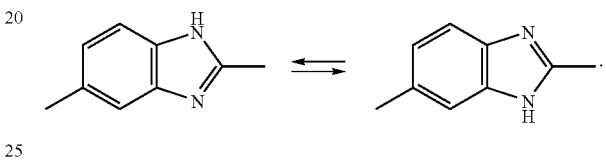

The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, "Comprehensive Organic Transformations", VCH Publishers (1989); T. W. Greene and P. G. M. Wuts, "Protective Groups in Organic Synthesis", 3$^{rd}$ edition, John Wiley and Sons (1999); L. Fieser and M. Fieser, "Fieser and Fieser's Reagents for Organic Synthesis", John Wiley and Sons (1994); A. Katritzky and A. Pozharski, "Handbook of Heterocyclic Chemistry", 2$^{nd}$ edition (2001); M. Bodanszky, A. Bodanszky, "The Practice of Peptide Synthesis", Springer-Verlag, Berlin Heidelberg (1984); J. Seyden-Penne, "Reductions by the Alumino- and Borohydrides in Organic Synthesis", 2$^{nd}$ edition, Wiley-VCH, (1997); and L. Paquette, editor, "Encyclopedia of Reagents for Organic Synthesis", John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

These detailed descriptions fall within the scope, and serve to exemplify, the above-described General Synthetic Procedures which form part of the invention. These detailed descriptions are presented for illustrative purposes only and are not intended as a restriction on the scope of the invention.

Method 1.

General scheme.

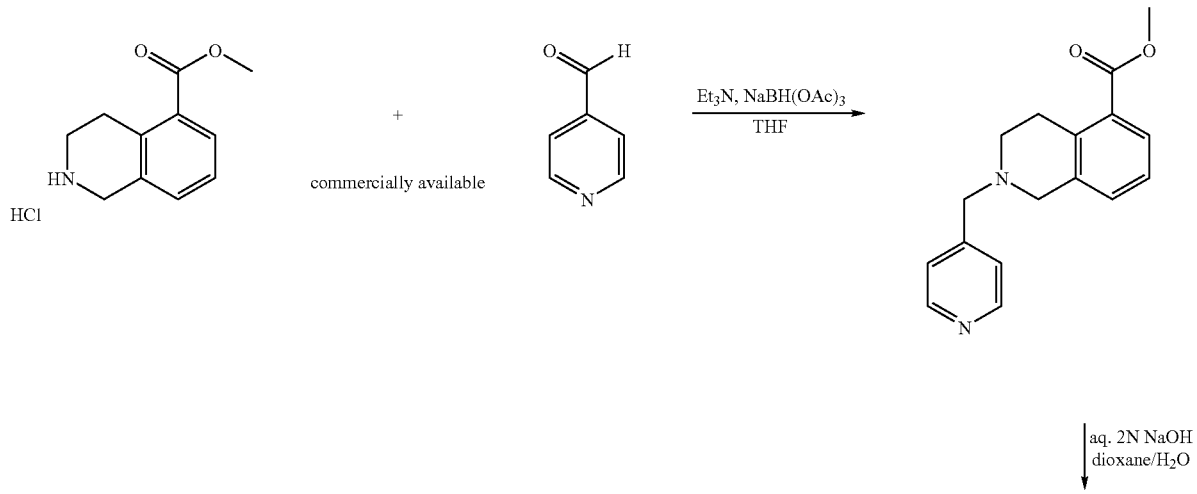

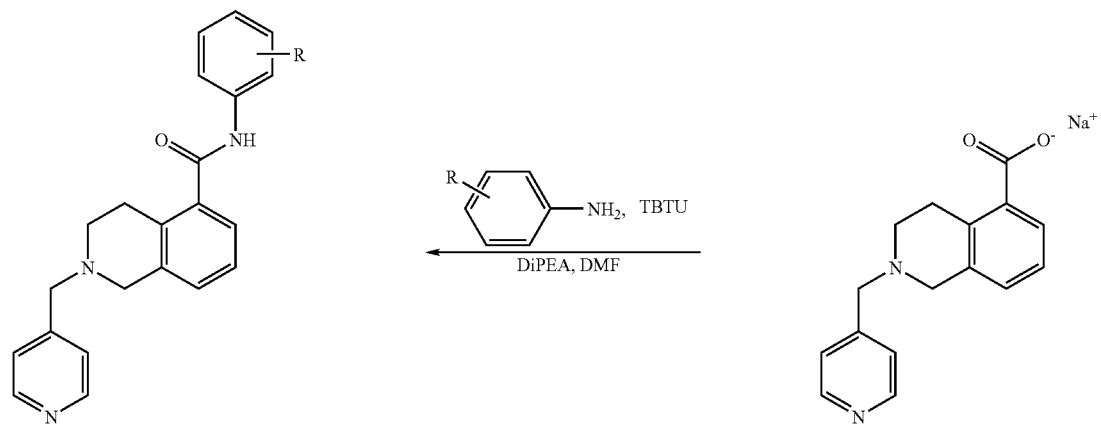

Example 1

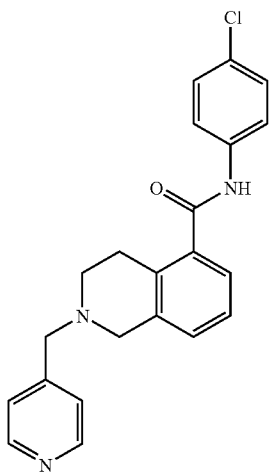

N-(4-chlorophenyl)-2-(pyridin-4-ylmethyl)-1,2,3,4-tetrahydroisoquinoline-5-carboxamide Step (a) Preparation of methyl 2-(pyridine-4-ylmethyl)-1,2,3,4-tetrahydroisoquinoline-5-carboxylate 5-Methoxycarbonyl-1,2,3,4-tetrahydroisoquinoline hydrochloride (1 g, 4.39 mmol) and triethylamine (666 mg, 6.58 mmol) were mostly dissolved in tetrahydrofuran (30 mL). 4-Pyridinecarboxaldehyde (494 mg, 4.61 mmol) and sodium triacetoxyborohydride (1.3 g, 6.15 mmol) were then added to the mixture. The reaction mixture was stirred at room temperature overnight. The reaction was quenched with saturated aqueous sodium bicarbonate. The tetrahydrofuran was removed under vacuum and the remaining residue was dissolved in ethyl acetate then washed with saturated aqueous sodium bicarbonate and brine. The organic layer was dried over sodium sulfate and concentrated under vacuum to give 1.29 g of methyl 2-(pyridine-4-ylmethyl)-1,2,3,4-tetrahydroisoquinoline-5-carboxylate as a light yellow oil. MS (ESI, pos. ion) m/z: 283.0 (M+1).

Step (b) Preparation of Sodium 2-(pyridin-4-ylmethyl)-1,2,3,4-tetrahydroisoquinoline-5-carboxylate Methyl 2-(pyridine-4-ylmethyl)-1,2,3,4-tetrahydroisoquinoline-5-carboxylate (1.14 g, 4.04 mmol) was dissolved in dioxane (15 mL) and water (5 mL) then added a solution of 2N aqueous sodium hydroxide (2.22 mL, 4.45 mmol). The reaction mixture was stirred at room temperature for 2 days then concentrated under vacuum. The remaining oil was azeotroped with toluene and dried under high vacuum to afford 1.25 g of sodium 2-(pyridin-4-ylmethyl)-1,2,3,4-tetrahydroisoquinoline-5-carboxylate as a pale yellow oil/foam. MS (ESI, pos. ion) m/z: 269.0 (M+1).

Step (c) Preparation of N-(4-chlorophenyl)-2-(pyridin-4-ylmethyl)-1,2,3,4-tetrahydroisoquinoline-5-carboxamide Sodium 2-(pyridin-4-ylmethyl)-1,2,3,4-tetrahydroisoquinoline-5-carboxylate (80 mg, 0.276 mmol) was dissolved in N,N-dimethylformamide (1 mL) then added 4-chloroaniline (42 mg, 0.331 mmol), 2-(1H-benzotriazol-1-yl)-1,1,3,3-tetramethyluronium tetrafluoroborate (133 mg, 0.414 mmol), and N,N-diisopropylethylamine (56 mg, 0.552 mmol). The reaction mixture was stirred at room temperature overnight. The mixture was concentrated under vacuum. The remaining orange oil was purified by silica gel chromatography (1% to 3% 7N ammonia in methanol/dichloromethane) to afford N-(4-chlorophenyl)-2-(pyridin-4-ylmethyl)-1,2,3,4-tetrahydroisoquinoline-5-carboxamide (89 mg) as a light yellow solid. MS (ESI, pos. ion) m/z: 378.0 (M+1).

The following compounds were synthesized as described in Method 1. In each case, the appropriate aniline was used in the final coupling step.

| Ex. | Structure | Method of Synthesis | MS (ESI, pos. ion) m/z (M + H) |
|---|---|---|---|
| 1A | 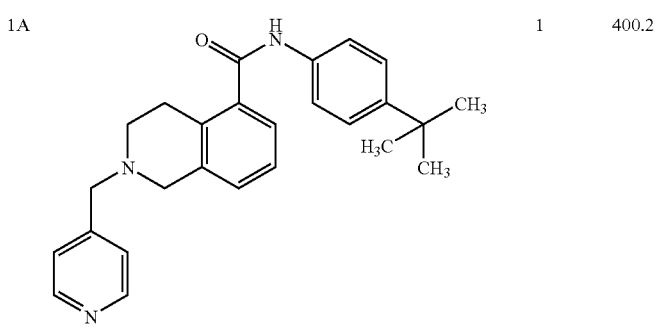 | 1 | 400.2 |

-continued

| Ex. | Structure | Method of Synthesis | MS (ESI, pos. ion) m/z (M + H) |
|---|---|---|---|
| 1B | 2-(pyridin-4-ylmethyl)-1,2,3,4-tetrahydroisoquinoline-5-carboxylic acid (3-methoxyphenyl)amide | 1 | 374.1 |
| 1C | 2-(pyridin-4-ylmethyl)-1,2,3,4-tetrahydroisoquinoline-5-carboxylic acid (3-methylphenyl)amide | 1 | 358.2 |
| 1D | 2-(pyridin-4-ylmethyl)-1,2,3,4-tetrahydroisoquinoline-5-carboxylic acid (3,5-dimethoxyphenyl)amide | 1 | 404.2 |

Method 2.

General scheme.

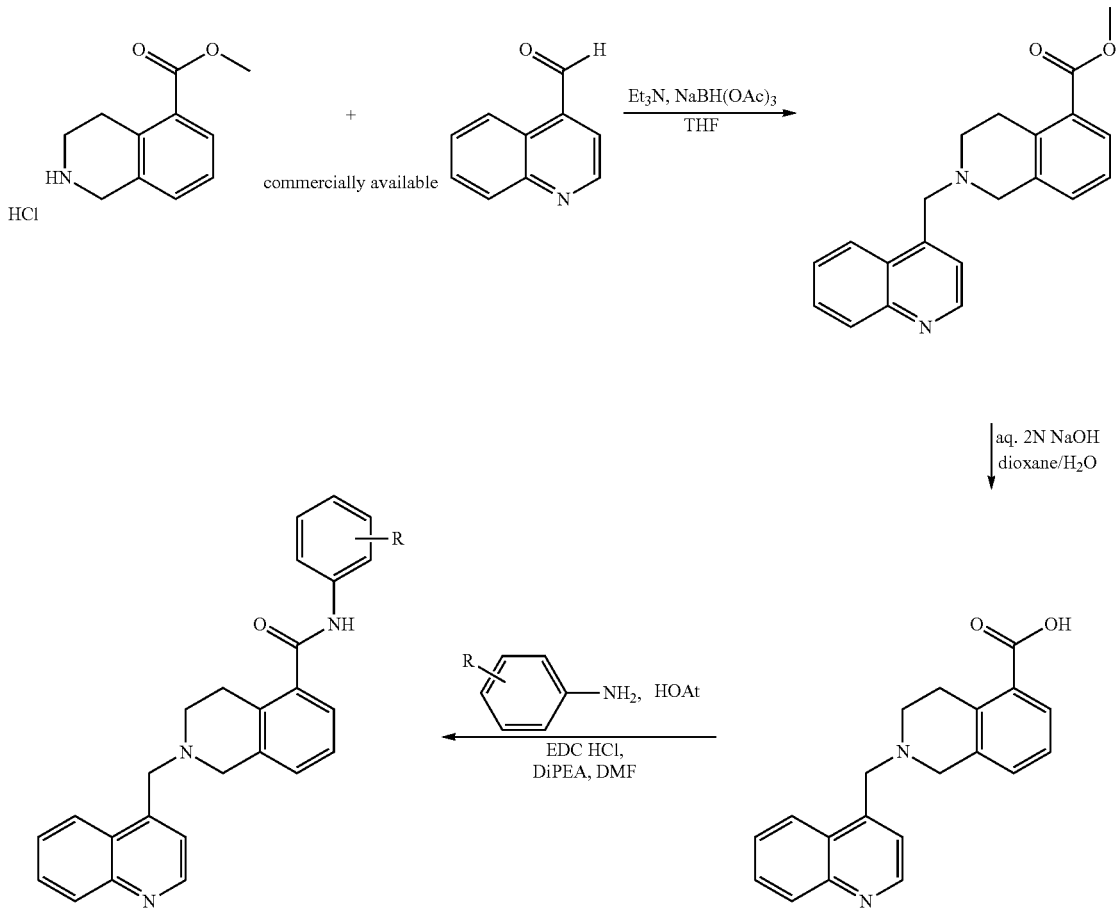

Example 2

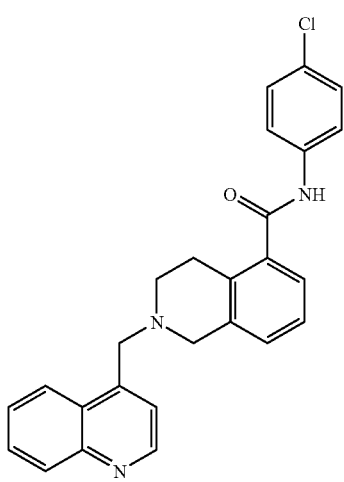

N-(4-chlorophenyl)-2-(quinolin-4-ylmethyl)-1,2,3,4-tetrahydroisoquinoline-5-carboxamide Step (a) Preparation of methyl 2-(quinolin-4-ylmethyl)-1,2,3,4-tetrahydroisoquinoline-5-carboxylate The starting material, methyl 2-(quinolin-4-ylmethyl)-1,2,3,4-tetrahydroisoquinoline-5-carboxylate, was prepared using a similar method to that described above for Method 1, step (a). 4-Quinolinecarboxaldehyde was used as the aldehyde source for this reaction.

Step (b) Preparation of 2-(quinolin-4-ylmethyl)-1,2,3,4-tetrahydroisoquinoline-5-carboxylic Acid Methyl 2-(quinolin-4-ylmethyl)-1,2,3,4-tetrahydroisoquinoline-5-carboxylate (1.2 g, 3.61 mmol) was dissolved in dioxane (15 mL) and water (5 mL) then added a solution of 2N aqueous sodium hydroxide (1.90 mL, 3.80 mmol). The reaction mixture was stirred at room temperature for 2 days then concentrated under vacuum to remove the dioxane. The remaining aqueous solution was diluted with water then added 1N aqueous hydrochloric acid (3.8 mL) to bring the mixture to pH 7. A precipitate formed which was collected on a glass frit, washing with minimal water then dichloromethane. The solid was dried under high vacuum to afford 1.06 g of 2-(quinolin-4-ylmethyl)-1,2,3,4-tetrahydroisoquinoline-5-carboxylic acid as a white solid. MS (ESI, pos. ion) m/z: 319.1 (M+1).

Step (c) Preparation of N-(4-chlorophenyl)-2-(quinolin-4-ylmethyl)-1,2,3,4-tetrahydroisoquinoline-5-carboxamide 2-(Quinolin-4-ylmethyl)-1,2,3,4-tetrahydroisoquinoline-5-carboxylic acid (80 mg, 0.251 mmol) was suspended in N,N-dimethylformamide (1.2 mL) then added 4-chloroaniline (45 mg, 0.351 mmol), 1-hydroxy-7-azabenzotriazole (34 mg, 0.251 mmol), 1-(3-dimethylaminopropyl)-3-ethylcarbodiimide hydrochloride (72 mg, 0.376 mmol) and N,N-diisopropylethylamine (89 mg, 0.878 mmol). The reaction mixture was stirred at room temperature for two days then concentrated under vacuum. The crude material was purified by silica gel chromatography (50% to 67% ethyl acetate/hexane) to afford N-(4-chlorophenyl)-2-(quinolin-4-ylmethyl)-1,2,3,4-tetrahydroisoquinoline-5-carboxamide (92 mg) as a white solid. MS (ESI, pos. ion) m/z: 428.1 (M+1).

Example 3

N-(3,3-dimethylindolin-6-yl)-2-(quinolin-4-ylmethyl)-1,2,3,4-tetrahydroisoquinoline-5-carboxamide Preparation of N-(1-acetyl-3,3-dimethylindolin-6-yl)-2-(quinolin-4-ylmethyl)-1,2,3,4-tetrahydroisoquinoline-5-carboxamide N-(1-acetyl-3,3-dimethylindolin-6-yl)-2-(quinolin-4-ylmethyl)-1,2,3,4-tetrahydroisoquinoline-5-carboxamide was prepared as described in Method 2.

Preparation of N-(3,3-dimethylindolin-6-yl)-2-(quinolin-4-ylmethyl)-1,2,3,4-tetrahydroisoquinoline-5-carboxamide N-(1-Acetyl-3,3-dimethylindolin-6-yl)-2-(quinolin-4-ylmethyl)-1,2,3,4-tetrahydroisoquinoline-5-carboxamide (55 mg, 0.109 mmol) was mostly dissolved in ethanol (1.25 mL) then added concentrated hydrochloric acid (0.745 mL). The reaction mixture was heated at 60° C. for 6 hours. The mixture was concentrated under vacuum and the remaining residue diluted with a small amount of water. The solution was brought to pH 9-10 with the addition of 6N aqueous sodium hydroxide. A precipitate formed which was collected on a glass frit, washing with minimal water then dichloromethane. The solid was dried under high vacuum to afford 35 mg of N-(3,3-dimethylindolin-6-yl)-2-(quinolin-4-ylmethyl)-1,2,3,4-tetrahydroisoquinoline-5-carboxamide as a tan solid. MS (ESI, pos. ion) m/z: 463.2 (M+1)

The following compounds were synthesized as described in Method 2. In each case, the appropriate aniline was used in the final coupling step.

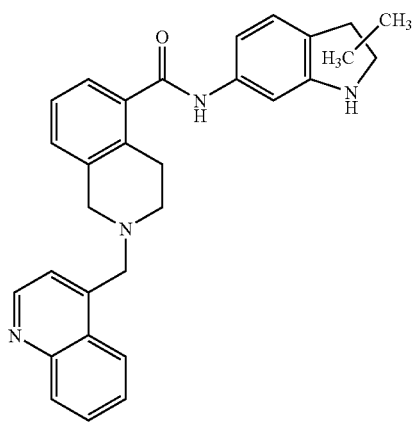

| Ex. | Structure | Method of Synthesis | MS (ESI, pos. ion) m/z (M + H) |
|---|---|---|---|
| 3A | 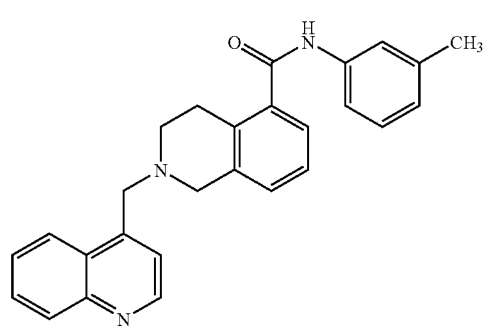 | 2 | 408.2 |

-continued

| Ex. | Structure | Method of Synthesis | MS (ESI, pos. ion) m/z (M + H) |
|---|---|---|---|
| 3B | *N-(3-methoxyphenyl)-2-(quinolin-4-ylmethyl)-1,2,3,4-tetrahydroisoquinoline-5-carboxamide* | 2 | 424.2 |
| 3C | *N-(3,5-dimethoxyphenyl)-2-(quinolin-4-ylmethyl)-1,2,3,4-tetrahydroisoquinoline-5-carboxamide* | 2 | 454.2 |
| 3D | *N-(4-tert-butylphenyl)-2-(quinolin-4-ylmethyl)-1,2,3,4-tetrahydroisoquinoline-5-carboxamide* | 2 | 450.2 |
| 3E | *N-(3,4-dimethylphenyl)-2-(quinolin-4-ylmethyl)-1,2,3,4-tetrahydroisoquinoline-5-carboxamide* | 2 | 422.2 |

-continued

| Ex. | Structure | Method of Synthesis | MS (ESI, pos. ion) m/z (M + H) |
|-----|-----------|---------------------|--------------------------------|
| 3F  | 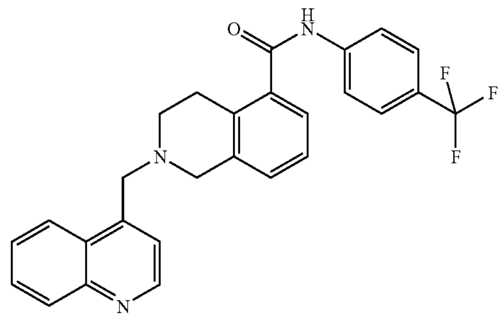          | 2                   | 462.1                          |
| 3G  | 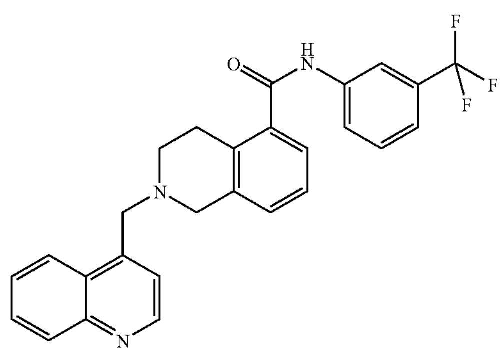          | 2                   | 462.2                          |
| 3H  | 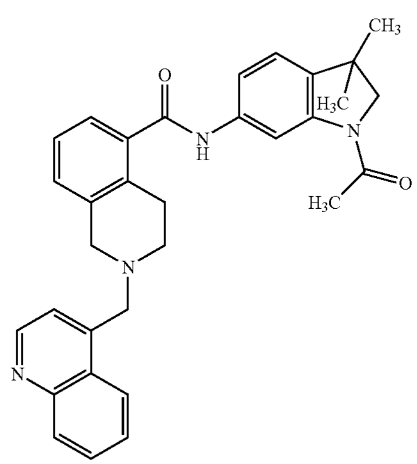          | 2                   | 505.2                          |

Example 4

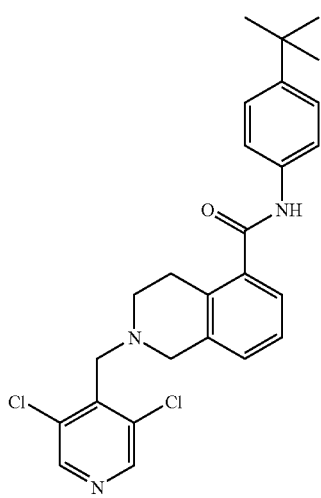

N-(4-tert-butylphenyl)-2-((3,5-dichloropyridin-4-yl)methyl)-1,2,3,4-tetrahydroisoquinoline-5-carboxamide N-(4-tert-Butylphenyl)-2-((3,5-dichloropyridin-4-yl)methyl)-1,2,3,4-tetrahydroisoquinoline-5-carboxamide, was prepared using a similar method to that described in Method 1. In step (a), 3,5-dichloro-4-pyridinecarboxaldehyde was used as the aldehyde source and in step (b) the reaction was heated to 40° C. overnight. MS (ESI, pos. ion) m/z: 468.1 (M+1).

Method 3.

General scheme.

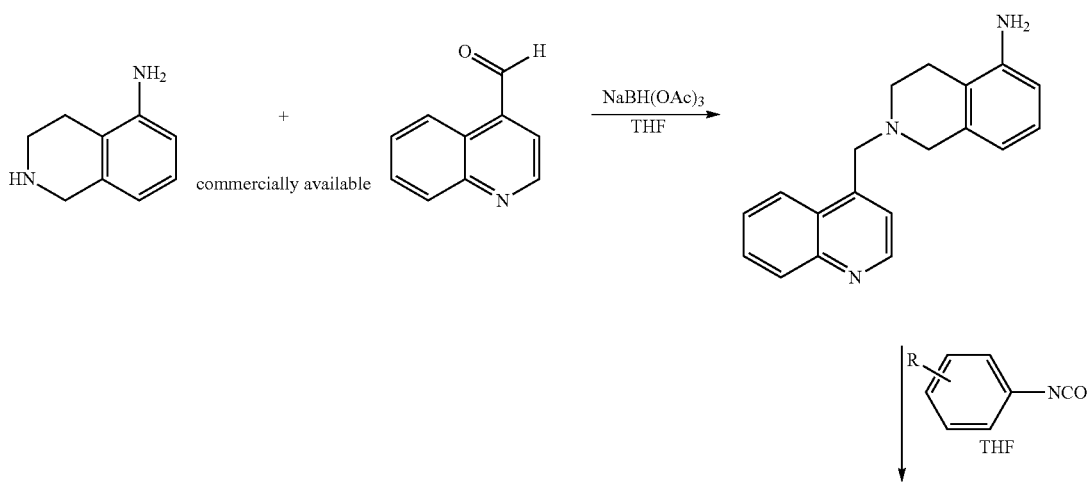

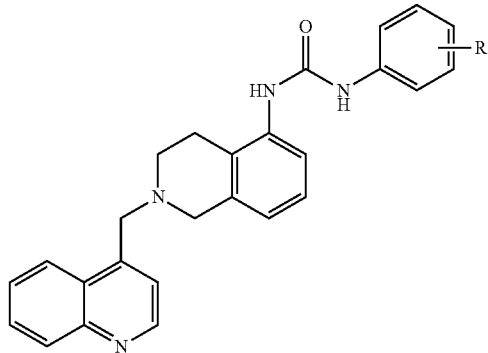

Example 5

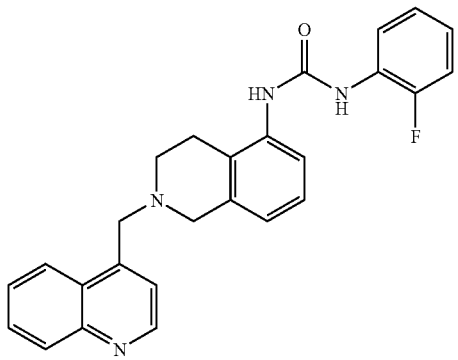

1-(2-fluorophenyl)-3-(2-(quinolin-4-ylmethyl)-1,2,3,4-tetrahydroisoquinolin-5-yl)urea Step (a) Preparation of 2-(quinolin-4-ylmethyl)-1,2,3,4-tetrahydroisoquinolin-5-amine 1,2,3,4-tetrahydro-5-aminoisoquinoline (500 mg, 3.37 mmol) was dissolved in tetrahydrofuran (15 mL) then added 4-quinolinecarboxaldehyde (556 mg, 3.54 mmol) and sodium triacetoxyborohydride (786 mg, 3.71 mmol). The reaction mixture was stirred at room temperature overnight. The reaction was quenched with saturated aqueous sodium bicarbonate then concentrated under vacuum. The remaining residue was dissolved in ethyl acetate then washed with saturated aqueous sodium bicarbonate and brine. The organic layer was dried over sodium sulfate and concentrated under vacuum. The crude material was purified by silica gel chromatography (50% to 80% ethyl acetate/hexane) to afford 2-(quinolin-4-ylmethyl)-1,2,3,4-tetrahydroisoquinolin-5-amine (805 mg) as a yellow solid. MS (ESI, pos. ion) m/z: 290.1 (M+1).

Step (b) Preparation of 1-(2-fluorophenyl)-3-(2-(quinolin-4-ylmethyl)-1,2,3,4-tetrahydroisoquinolin-5-yl)urea 2-(Quinolin-4-ylmethyl)-1,2,3,4-tetrahydroisoquinolin-5-amine (80 mg, 0.277 mmol) was suspended in tetrahydrofuran (1 mL) then added a solution of 2-fluorophenylisocyanate (38 mg, 0.277 mmol) in tetrahydrofuran (0.5 mL). The reaction mixture was stirred at room temperature for 2 days. The product had precipitated from the reaction mixture and was collected on a glass frit, washing with minimal tetrahydrofuran then dichloromethane. The solid was dried under high vacuum to give 78 mg of 1-(2-fluorophenyl)-3-(2-(quinolin-4-ylmethyl)-1,2,3,4-tetrahydroisoquinolin-5-yl)urea as a white solid. MS (ESI, pos. ion) m/z: 427.1 (M+1).

The following compounds were synthesized using Method 3. In each case, the appropriate isocyanate was used in the final step. If precipitation of the final compound did not occur, purification by silica gel chromatography was used.

| Ex. | Structure | Method of Synthesis | MS (ESI, pos. ion) m/z (M + H) |
|---|---|---|---|
| 5A | 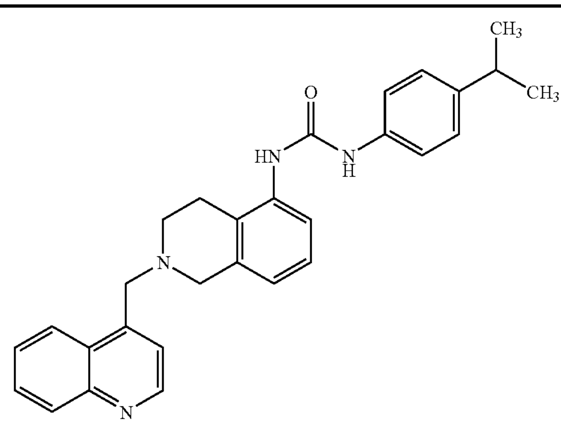 | 3 | 451.2 |
| 5B | 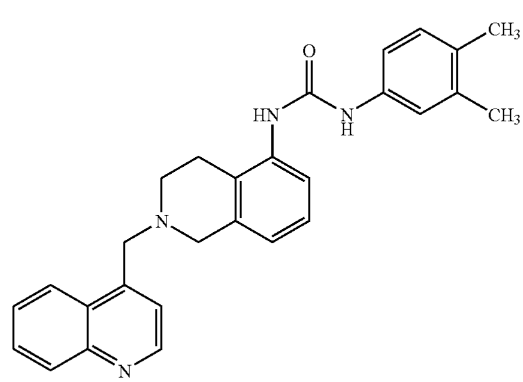 | 3 | 437.2 |

-continued
| Ex. | Structure | Method of Synthesis | MS (ESI, pos. ion) m/z (M + H) |
|---|---|---|---|
| 5C | 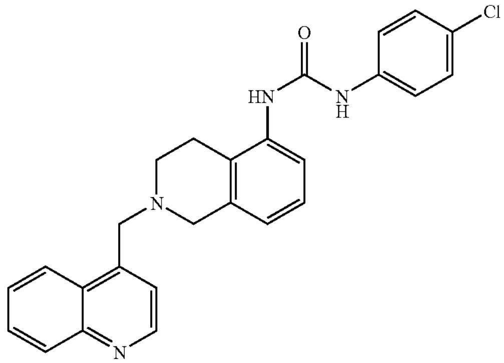 | 3 | 443.1 |
| 5D | 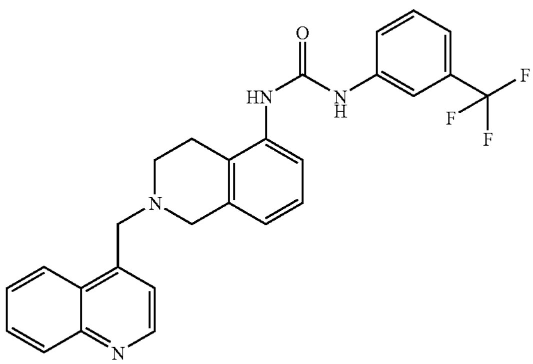 | 3 | 477.2 |
Method 4.
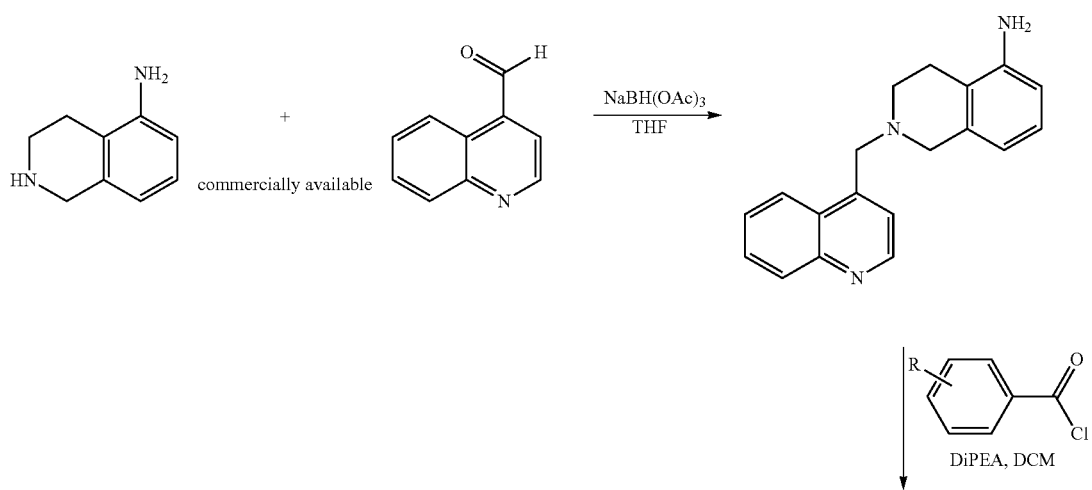
General scheme.

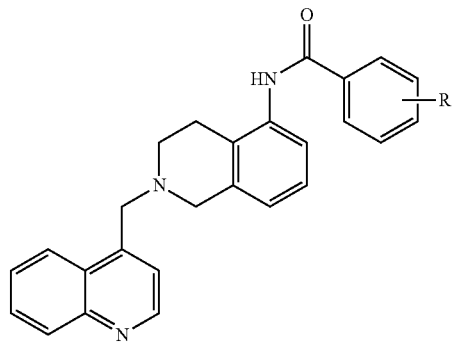

Example 6

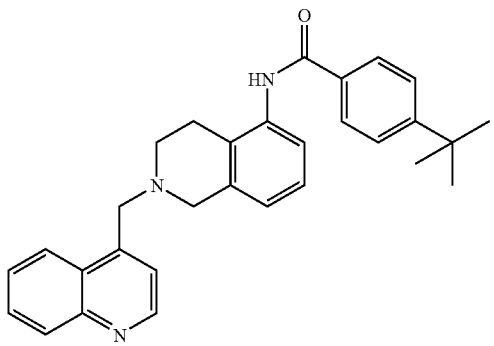

4-tert-butyl-N-(2-(quinolin-4-ylmethyl)-1,2,3,4-tetrahydroisoquinolin-5-yl)benzamide Step (a) Preparation of 2-(quinolin-4-ylmethyl)-1,2,3,4-tetrahydroisoquinolin-5-amine The starting material, 2-(quinolin-4-ylmethyl)-1,2,3,4-tetrahydroisoquinolin-5-amine was prepared as described previously in Method 3, step (a).

Step (b) Preparation of 4-tert-butyl-N-(2-(quinolin-4-ylmethyl)-1,2,3,4-tetrahydroisoquinolin-5-yl)benzamide 2-(Quinolin-4-ylmethyl)-1,2,3,4-tetrahydroisoquinolin-5-amine (80 mg, 0.277) was suspended in dichloromethane (1 mL) then added a solution of 4-tert-butylbenzylchloride (57 mg, 0.291 mmol) in dichloromethane (0.5 mL) and N,N-diisopropylethylamine (56 mg, 0.554 mmol). The reaction mixture was stirred at room temperature for 2 days. The reaction mixture was purified directly using silica gel chromatography (40% to 60% ethyl acetate/hexane) to afford 4-tert-butyl-N-(2-(quinolin-4-ylmethyl)-1,2,3,4-tetrahydroisoquinolin-5-yl)benzamide (107 mg) as a light yellow solid. MS (ESI, pos. ion) m/z: 450.2 (M+1).

The following compounds were synthesized using Method 4. In each case, the appropriate benzylchloride was used in the last step.

| Ex. | Structure | Method of Synthesis | MS (ESI, pos. ion) m/z (M + H) |
|---|---|---|---|
| 6A | (3,4-dimethylbenzamide derivative) | 4 | 422.2 |

| Ex. | Structure | Method of Synthesis | MS (ESI, pos. ion) m/z (M + H) |
|---|---|---|---|
| 6B | 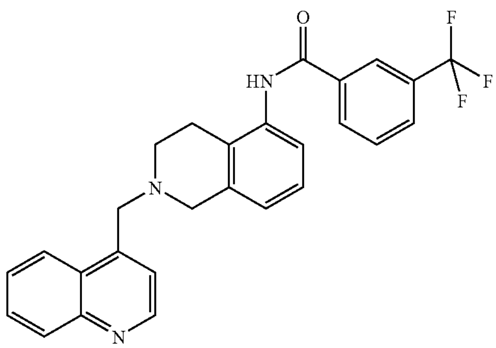 | 4 | 462.2 |
| 6C | 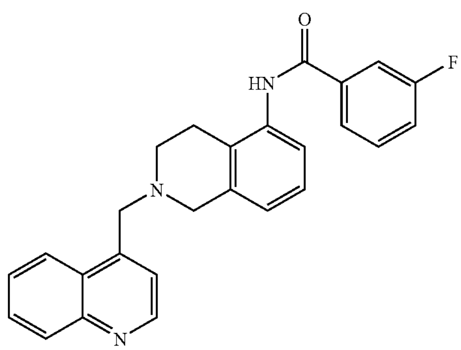 | 4 | 412.2 |
| 6D | 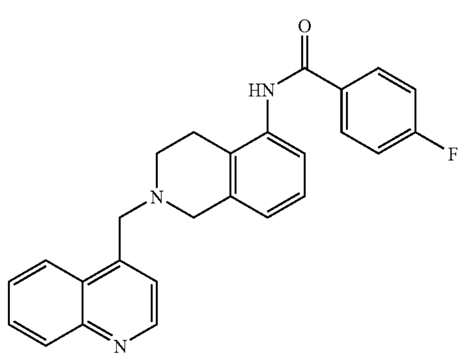 | 4 | 412.1 |

Method 5.

General scheme.

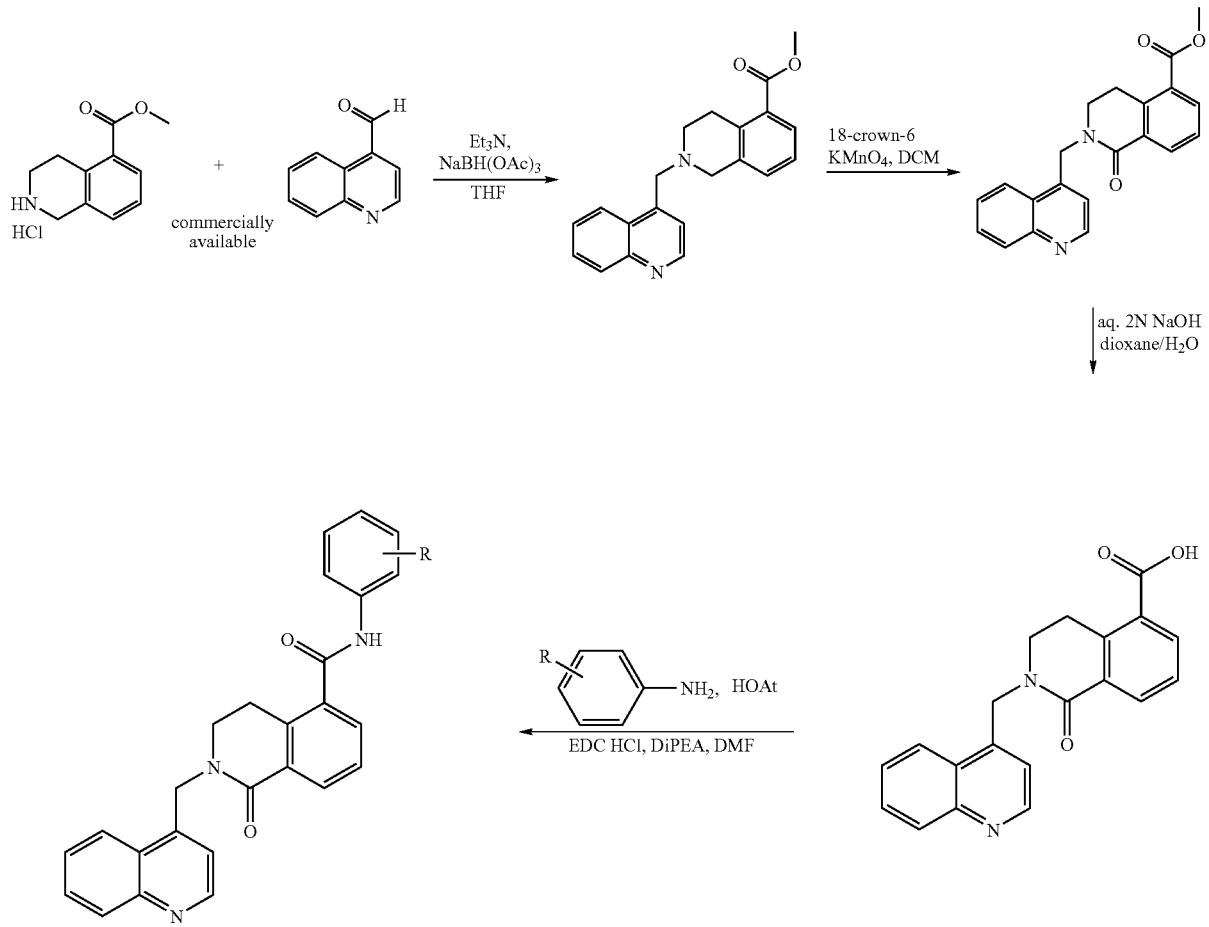

Example 7

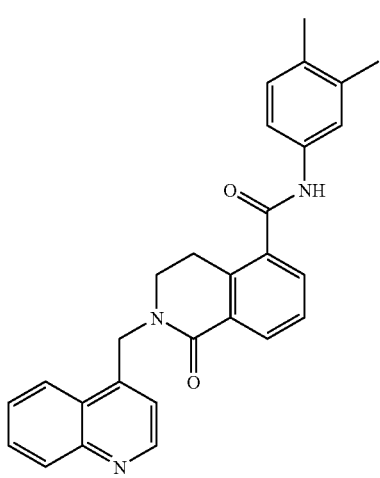

N-(3,4-dimethylphenyl)-1-oxo-2-(quinolin-4-ylmethyl)-1,2,3,4-tetrahydroisoquinoline-5-carboxamide Step (a) Preparation of methyl 2-(pyridine-4-ylmethyl)-1,2,3,4-tetrahydroisoquinoline-5-carboxylate Methyl 2-(pyridine-4-ylmethyl)-1,2,3,4-tetrahydroisoquinoline-5-carboxylate was prepared as described previously in Method 1, step (a).

Step (b) Preparation of methyl 1-oxo-2-(quinolin-4-ylmethyl)-1,2,3,4-tetrahydroisoquinoline-5-carboxylate Step (b) Preparation of methyl 1-oxo-2-(quinolin-4-ylmethyl)-1,2,3,4-tetrahydroisoquinoline-5-carboxylate Methyl 2-(pyridine-4-ylmethyl)-1,2,3,4-tetrahydroisoquinoline-5-carboxylate (500 mg, 1.51 mmol) was dissolved in dichloromethane (5 mL) then added 18-crown-6 (40 mg, 0.151 mmol), followed by slow addition of potassium permanganate (358 mg, 2.26 mmol). The reaction mixture was stirred at room temperature overnight. The reaction was quenched with saturated aqueous sodium metabisulfite until the mixture became colorless. Aqueous 1N hydrochloric acid was added to the mixture until the precipitate dissolved and the mixture became clear. The reaction mixture was diluted with water then extracted with dichloromethane. The organic layer was washed with brine, dried over sodium sulfate and concentrated under vacuum. The crude material was purified by silica gel chromatography (67% to 75% ethyl acetate/hexane) to afford methyl 1-oxo-2-(quinolin-4-ylmethyl)-1,2,3,4-tetrahydroisoquinoline-5-carboxylate (395 mg) as a white solid. MS (ESI, pos. ion) m/z: 347.1 (M+1).

Step (c) Preparation of 1-oxo-2-(quinolin-4-ylmethyl)-1,2,3,4-tetrahydroisoquinoline-5-carboxylic acid 1-Oxo-2-(quinolin-4-ylmethyl)-1,2,3,4-tetrahydroisoquinoline-5-carboxylic acid was prepared as described previously in Method 2, step (b).

Step (d) Preparation of N-(3,4-dimethylphenyl)-1-oxo-2-(quinolin-4-ylmethyl)-1,2,3,4-tetrahydroisoquinoline-5-carboxamide N-(3,4-dimethylphenyl)-1-oxo-2-(quinolin-4-ylmethyl)-1,2,3,4-tetrahydroisoquinoline-5-carboxamide was prepared as described previously in Method 2, step (c), using 3,4-dimethylaniline. MS (ESI, pos. ion) m/z: 436.2 (M+1).

The following compounds were synthesized using Method 5. In each case, the appropriate aniline was used in the last step.

| Ex. | Structure | Method of Synthesis | MS (ESI, pos. ion) m/z (M + H) |
|---|---|---|---|
| 7A | 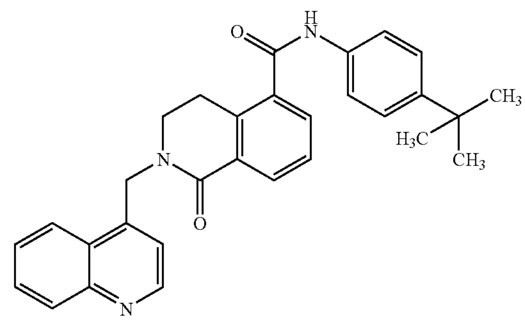 | 5 | 464.2 |
| 7B | 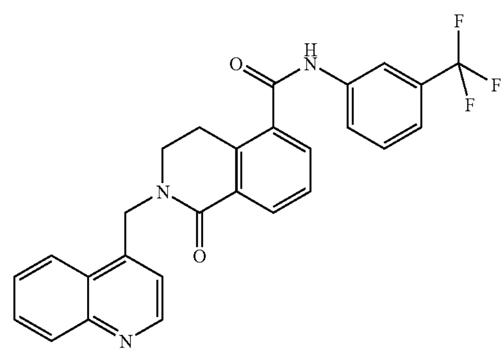 | 5 | 476.1 |

Method 6.

General scheme.

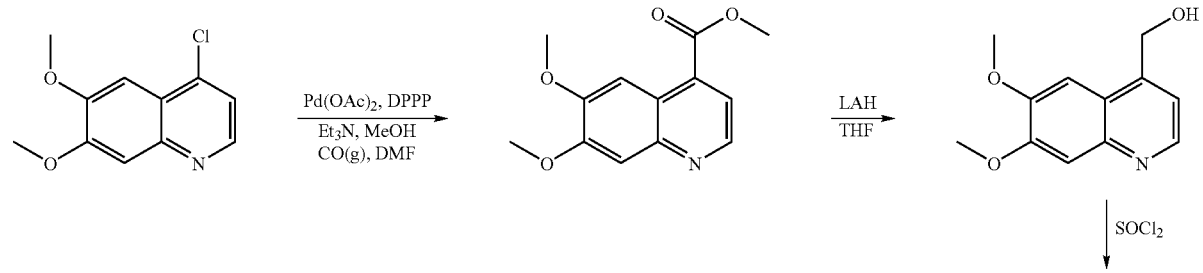

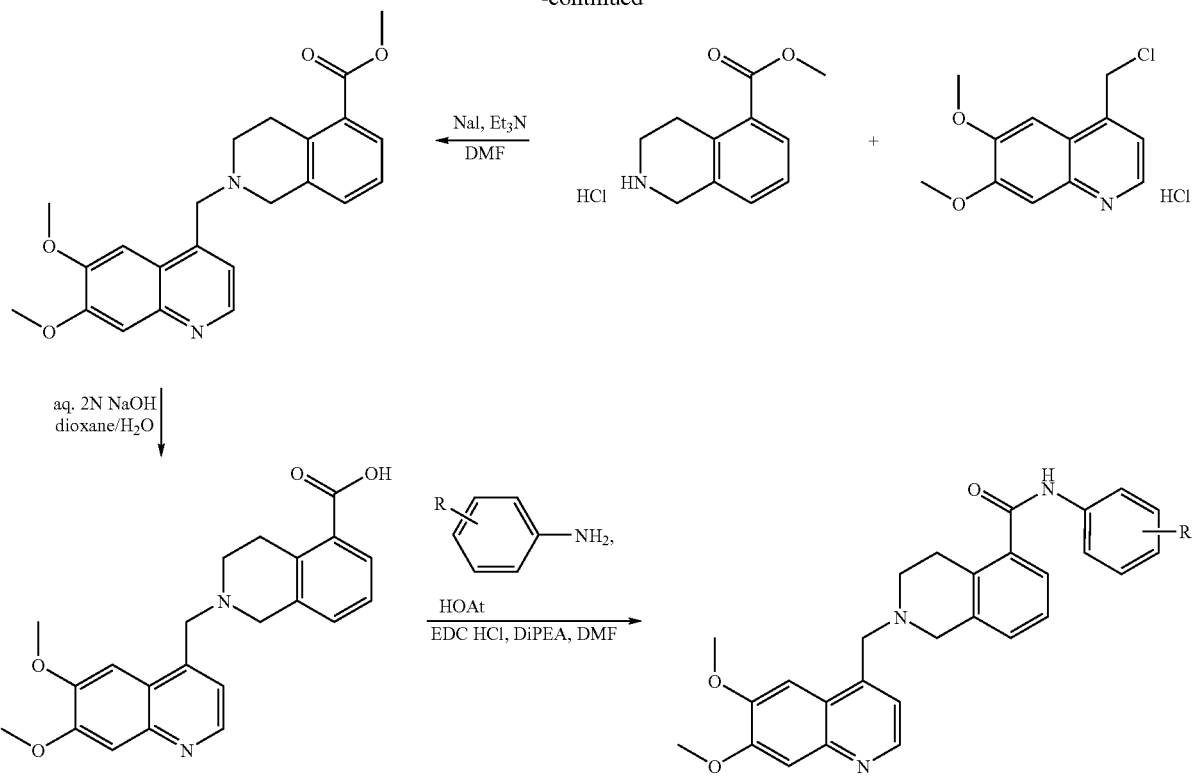

Example 8

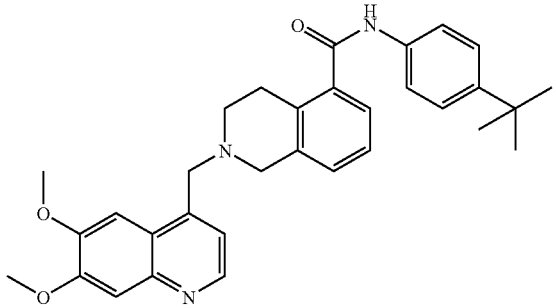

N-(4-tert-butylphenyl)-2-((6,7-dimethoxyquinoline-4-yl)methyl)-1,2,3,4-tetrahydroisoquinoline-5-carboxamide

Step (a) Preparation of methyl 6,7-dimethoxyquinoline-4-carboxylate

4-Chloro-6,7-dimethoxyquinoline (3 g, 13.45 mmol), palladium acetate (605 mg, 2.69 mmol) and 1,3-bis(diphenylphosphino)propane (1.39 g, 3.36 mmol) were added to a pressure tube then dissolved in N,N-dimethylformamide (25 mL). Carbon monoxide gas was bubbled through the mixture for 10-15 minutes. The reaction mixture was heated at 85° C. overnight. Additional palladium acetate (303 mg, 1.35 mmol), 1,3-bis(diphenylphosphino)propane (277 mg, 0.671 mmol) and methanol (2 mL) were added to the reaction mixture then carbon monoxide was bubbled through the solution for 10 minutes. The reaction mixture was then heated at 85° C. overnight again. The mixture was concentrated under vacuum. The crude material was purified twice by silica gel chromatography (1% methanol/dichloromethane then 50%-67% ethyl acetate/hexane) to afford methyl 6,7-dimethoxyquinoline-4-carboxylate (2.07 g) as a light yellow solid. MS (ESI, pos. ion) m/z: 248.0 (M+1).

Step (b) Preparation of (6,7-dimethoxyquinoline-4-yl)methanol

Lithium aluminum hydride (262 mg, 6.90 mmol) was suspended in tetrahydrofuran (20 mL) then cooled to −78° C. A solution of methyl 6,7-dimethoxyquinoline-4-carboxylate (1.55 g, 6.27 mmol) in tetrahydrofuran (20 mL) was added dropwise. The reaction mixture was stirred at −78° C. for 4 hours. The reaction was quenched with ethyl acetate (6 mL) then added sodium sulfate decahydrate and warmed the mixture to room temperature, stirring overnight. The mixture was filtered and the filtrate was concentrated under vacuum. The remaining solid was triturated with dichloromethane, filtered and dried under high vacuum to give 1.2 g of (6,7-dimethoxyquinoline-4-yl)methanol as a light yellow solid. MS (ESI, pos. ion) m/z: 220.0 (M+1).

Step (c) Preparation of 4-(chloromethyl)-6,7-dimethoxyquinoline hydrochloride (6,7-Dimethoxyquinolin-4-yl)methanol (1.11 g, 5.07 mmol) was dissolved in thionyl chloride (10 mL) at 0° C. The reaction mixture was stirred at 0° C. for 20 minutes then warmed to room temperature and stirred for 3.5 hours. The reaction mixture was diluted with benzene (20 ml) then concentrated under vacuum. The remaining solid was triturated with benzene then dried under high vacuum to afford 1.35 g of 4-(chloromethyl)-6,7-dimethoxyquinoline hydrochloride as a yellow solid. MS (ESI, pos. ion) m/z: 238.0 (M+1).

Step (d) Preparation of methyl 2-((6,7-dimethoxyquinolin-4-yl)methyl)-1,2,3,4-tetrahydroisoquinoline-5-carboxylate 5-Methoxycarbonyl-1,2,3,4-tetrahydroisoquinoline hydrochloride (582 mg, 2.56 mmol) was suspended in N,N-dimethylformamide (9 mL) then added triethylamine (833 mg, 8.23 mmol) and sodium iodide (137 mg, 0.915 mmol). The reaction mixture was stirred at room temperature overnight. The mixture was concentrated under vacuum and the residue dissolved in ethyl acetate. The organic layer was washed with saturated aqueous sodium bicarbonate and brine, dried over sodium sulfate and concentrated under vacuum to give (640 mg) of methyl 2-((6,7-dimethoxyquinolin-4-yl)methyl)-1,2,3,4-tetrahydroisoquinoline-5-carboxylate as a yellow foam. MS (ESI, pos. ion) m/z: 393.1 (M+1).

Step (e) Preparation of 2-((6,7-dimethoxyquinolin-4-yl)methyl)-1,2,3,4-tetrahydroisoquinoline-5-carboxylic acid 2-((6,7-dimethoxyquinolin-4-yl)methyl)-1,2,3,4-tetrahydroisoquinoline-5-carboxylic acid was prepared as described previously in Method 2, step (b).

Step (f) Preparation of N-(4-tert-butylphenyl)-2-((6,7-dimethoxyquinolin-4-yl)methyl)-1,2,3,4-tetrahydroisoquinoline-5-carboxamide N-(4-tert-butylphenyl)-2-((6,7-dimethoxyquinolin-4-yl)methyl)-1,2,3,4-tetrahydroisoquinoline-5-carboxamide was prepared as described in Method 2, step (c), using 4-tert-butylaniline. MS (ESI, pos. ion) m/z: 510.2 (M+1).

The following compounds were synthesized using Method 6. In each case, the appropriate aniline or amine was used in the last step.

| Ex. | Structure | Method of Synthesis | MS (ESI, pos. ion) m/z (M + H) |
|---|---|---|---|
| 8A | 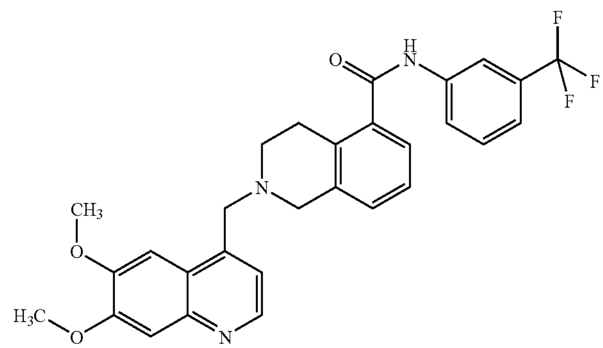 | 6 | 522.1 |
| 8B | 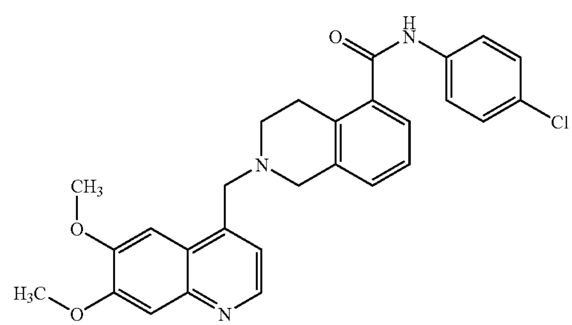 | 6 | 488.1 |
| 8C | 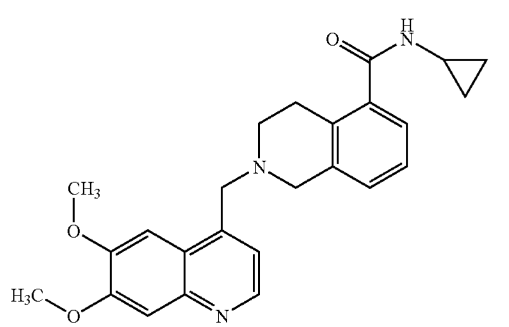 | 6 | 418.2 |

-continued

| Ex. | Structure | Method of Synthesis | MS (ESI, pos. ion) m/z (M + H) |
|---|---|---|---|
| 8D | 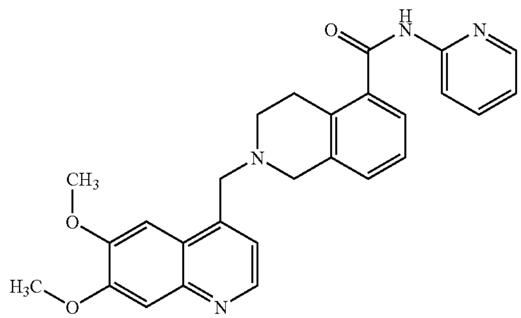 | 6 | 455.1 |
| 8E | 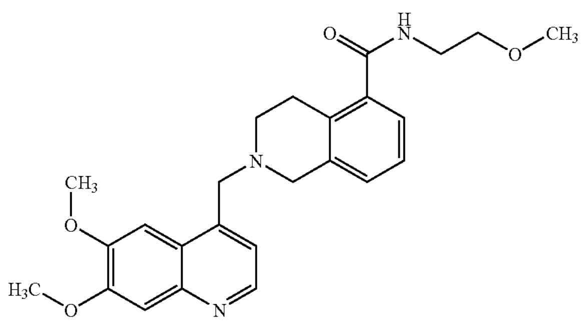 | 6 | 436.2 |
| 8F | 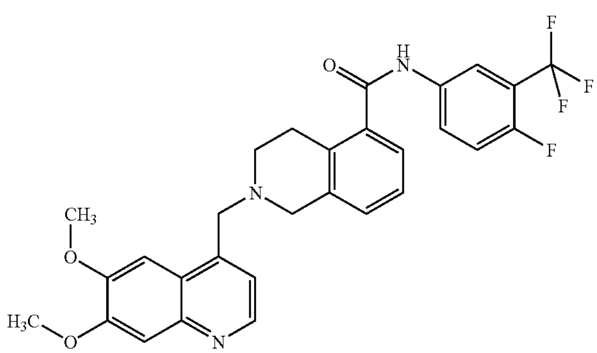 | 6 | 540.1 |
| 8G | 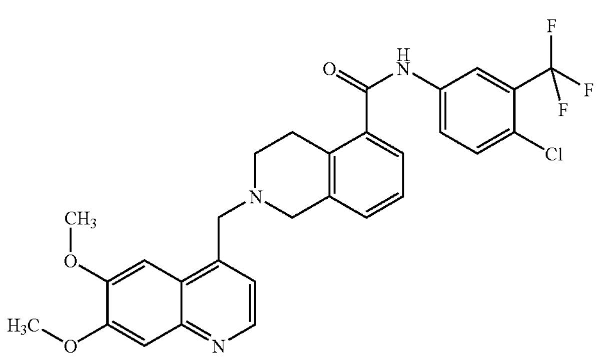 | 6 | 556.1 |

| Ex. | Structure | Method of Synthesis | MS (ESI, pos. ion) m/z (M + H) |
|---|---|---|---|
| 8H | 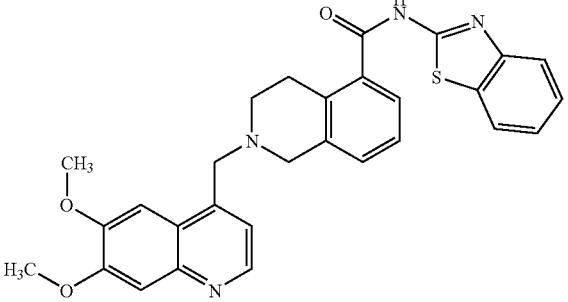 | 6 | 511.2 |
Method 7.
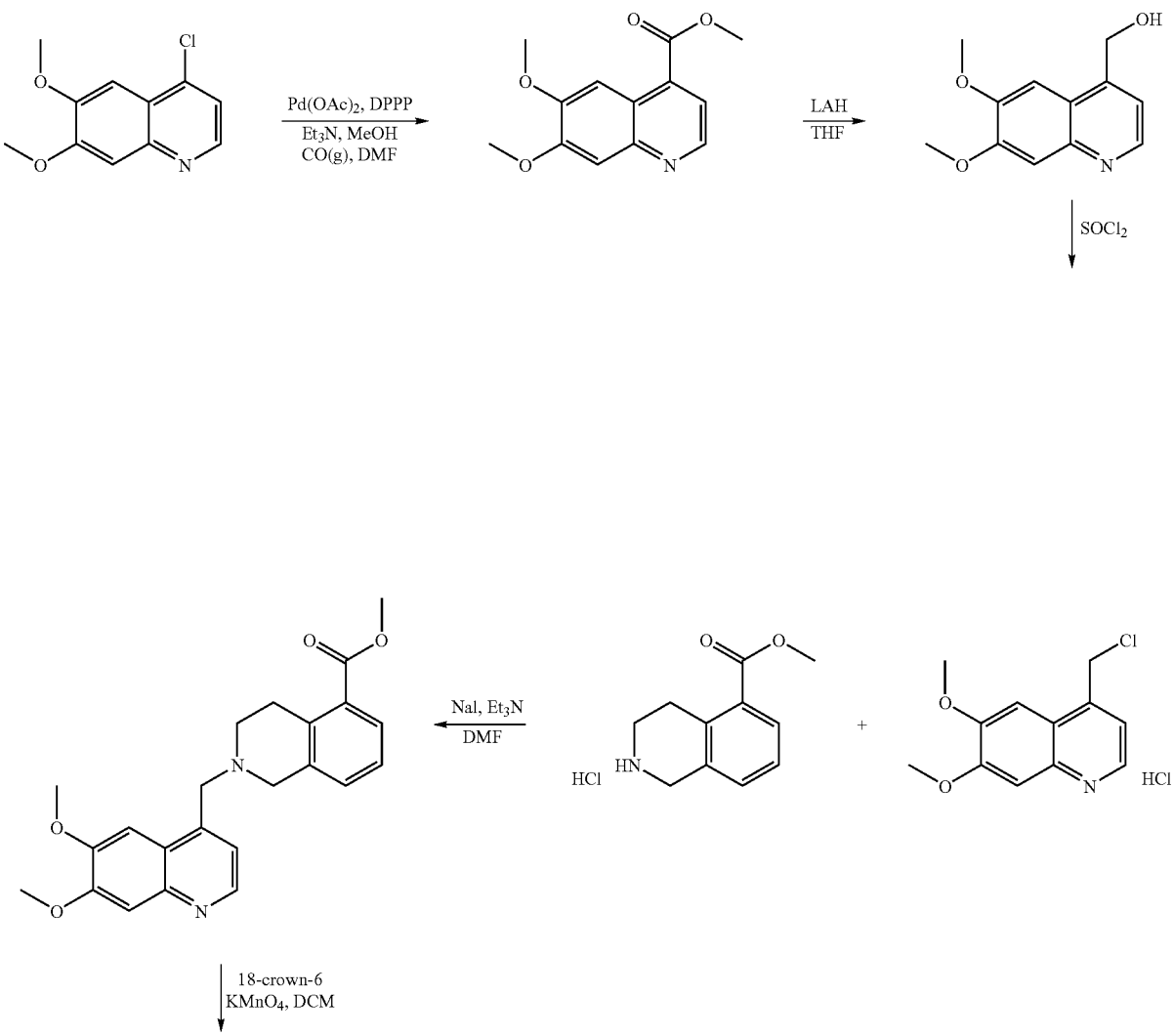
General scheme.

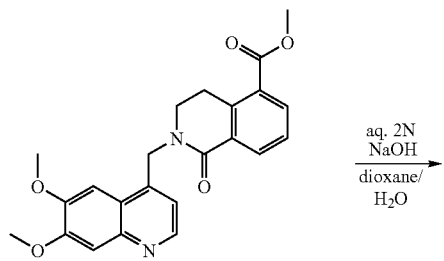

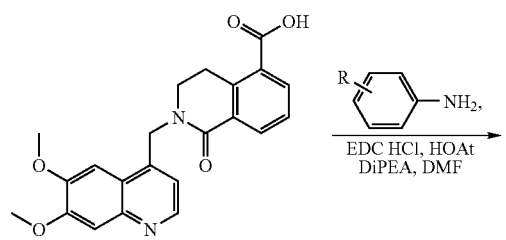

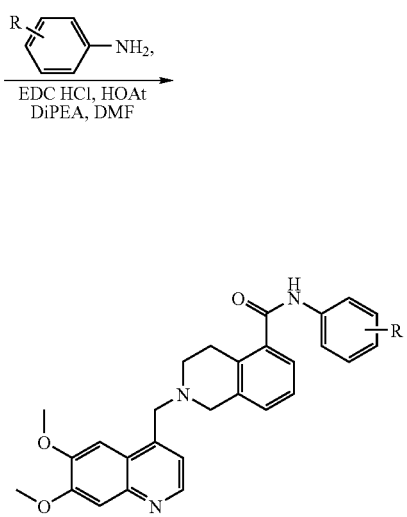

-continued

Example 9

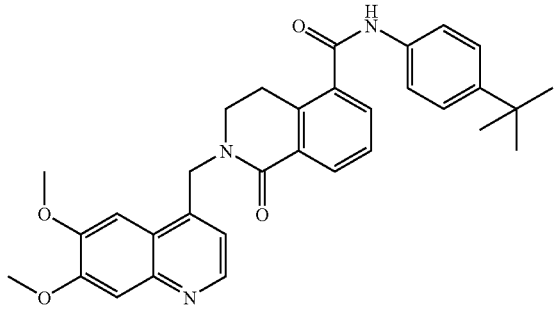

N-(4-tert-butylphenyl)-2-((6,7-dimethoxyquinolin-4-yl)methyl)-1-oxo-1,2,3,4-tetrahydroisoquinoline-5-carboxamide Preparation of methyl 2-((6,7-dimethoxyquinolin-4-yl)methyl)-1,2,3,4-tetrahydroisoquinoline-5-carboxylate Methyl 2-((6,7-dimethoxyquinolin-4-yl)methyl)-1,2,3,4-tetrahydroisoquinoline-5-carboxylate was prepared as previously described in Method 6.

Preparation of N-(4-tert-butylphenyl)-2-((6,7-dimethoxyquinolin-4-yl)methyl)-1-oxo-1,2,3,4-tetrahydroisoquinoline-5-carboxamide N-(4-tert-butylphenyl)-2-((6,7-dimethoxyquinolin-4-yl)methyl)-1-oxo-1,2,3,4-tetrahydroisoquinoline-5-carboxamide was prepared as previously described in Method 5. MS (ESI, pos. ion) m/z: 524.2 (M+1).

The following compound was synthesized as described in Method 7. The appropriate aniline was used in the last step.

| Ex. | Structure | Method of Synthesis | MS (ESI, pos. ion) m/z (M + H) |
|---|---|---|---|
| 9A | 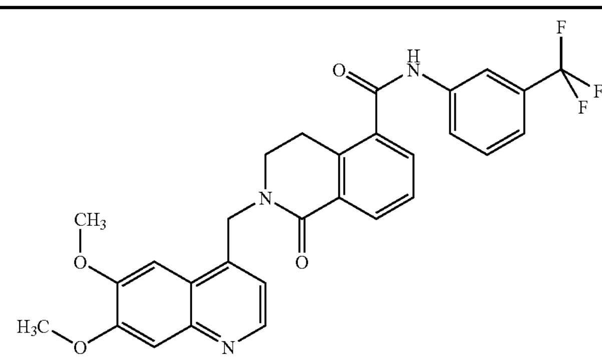 | 7 | 536.2 |

Method 8.
General Scheme.
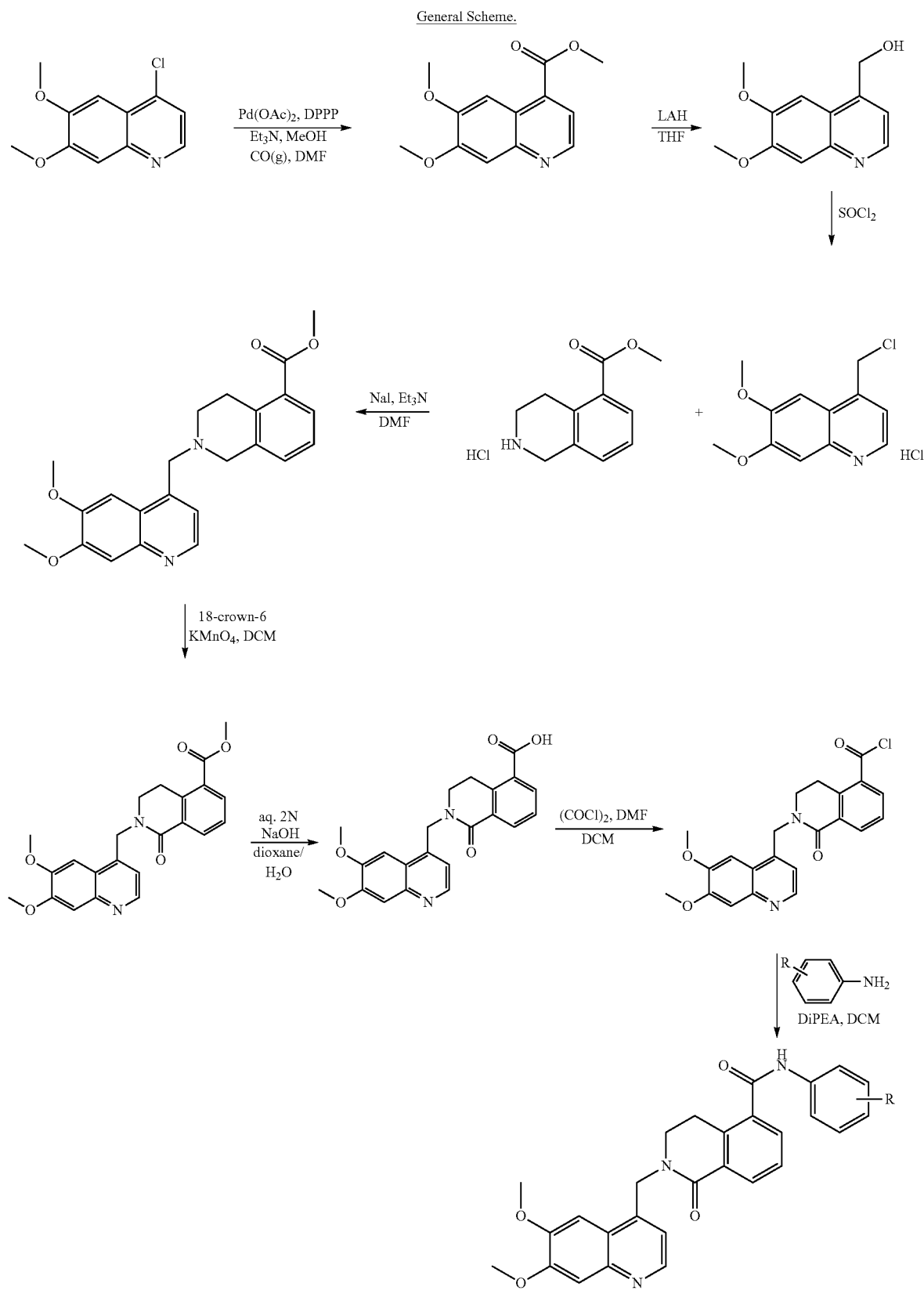

Example 10

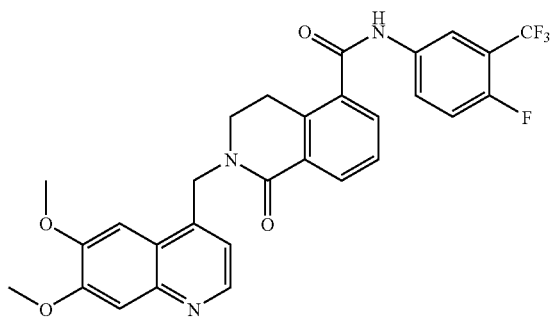

2-((6,7-dimethoxyquinolin-4-yl)methyl)-N-(4-fluoro-3-(trifluoromethyl)phenyl)-1-oxo-1,2,3,4-tetrahydroisoquinoline-5-carboxamide Preparation of 2-((6,7-dimethoxyquinolin-4-yl)methyl)-1-oxo-1,2,3,4-tetrahydroisoquinoline-5-carboxylic acid 2-((6,7-dimethoxyquinolin-4-yl)methyl)-1-oxo-1,2,3,4-tetrahydroisoquinoline-5-carboxylic acid was prepared as previously described in Method 7.

Preparation of 2-((6,7-dimethoxyquinolin-4-yl)methyl)-1-oxo-1,2,3,4-tetrahydroisoquinoline-5-carbonyl chloride 2-((6,7-dimethoxyquinolin-4-yl)methyl)-1-oxo-1,2,3,4-tetrahydroisoquinoline-5-carboxylic acid (126 mg, 0.321 mmol) was suspended in dichloromethane (4 mL) then added N,N-dimethylformamide (3-4 drops) and oxalyl chloride (0.442 mL, 0.643 mmol). The reaction mixture was stirred at room temperature for 4.5 hours. The mixture was concentrated under vacuum then dried under high vacuum overnight to afford 2-((6,7-dimethoxyquinolin-4-yl)methyl)-1-oxo-1,2,3,4-tetrahydroisoquinoline-5-carbonyl chloride (150 mg) as a light yellow solid. MS (ESI, pos. ion) m/z: 407.1 (M+1) for the methyl ester.

Preparation of 2-((6,7-dimethoxyquinolin-4-yl)methyl)-N-(4-fluoro-3-(trifluoromethyl)phenyl)-1-oxo-1,2,3,4-tetrahydroisoquinoline-5-carboxamide 2-((6,7-dimethoxyquinolin-4-yl)methyl)-1-oxo-1,2,3,4-tetrahydroisoquinoline-5-carbonyl chloride (75 mg, 0.168 mmol) was suspended in dichloromethane (1 mL) then added a solution of 4-fluoro-3-trifluoromethylaniline (36 mg, 0.201 mmol) in dichloromethane (0.5 mL) and N,N-diisopropylethylamine (65 mg, 0.504 mmol). The reaction mixture was stirred at room temperature for 2 days. The reaction mixture was purified directly by silica gel chromatography (3% methanol/dichloromethane) to afford 2-((6,7-dimethoxyquinolin-4-yl)methyl)-N-(4-fluoro-3-(trifluoromethyl)phenyl)-1-oxo-1,2,3,4-tetrahydroisoquinoline-5-carboxamide (46 mg) as a pale yellow solid. MS (ESI, pos. ion) m/z: 554.2 (M+1).

The following compound was synthesized using Method 8. The appropriate aniline was used in the final step.

| Ex. | Structure | Method of Synthesis | MS (ESI, pos. ion) m/z (M + H) |
|---|---|---|---|
| 10A | 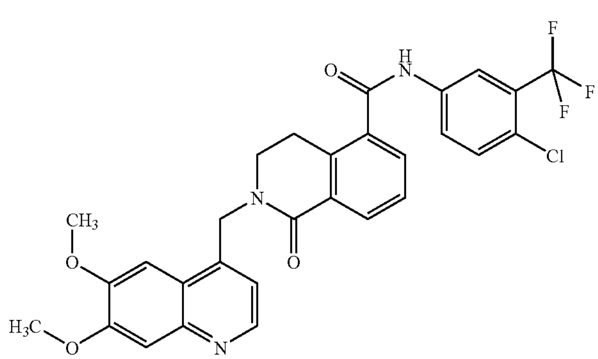 | 8 | 570.1 |

Method 9.

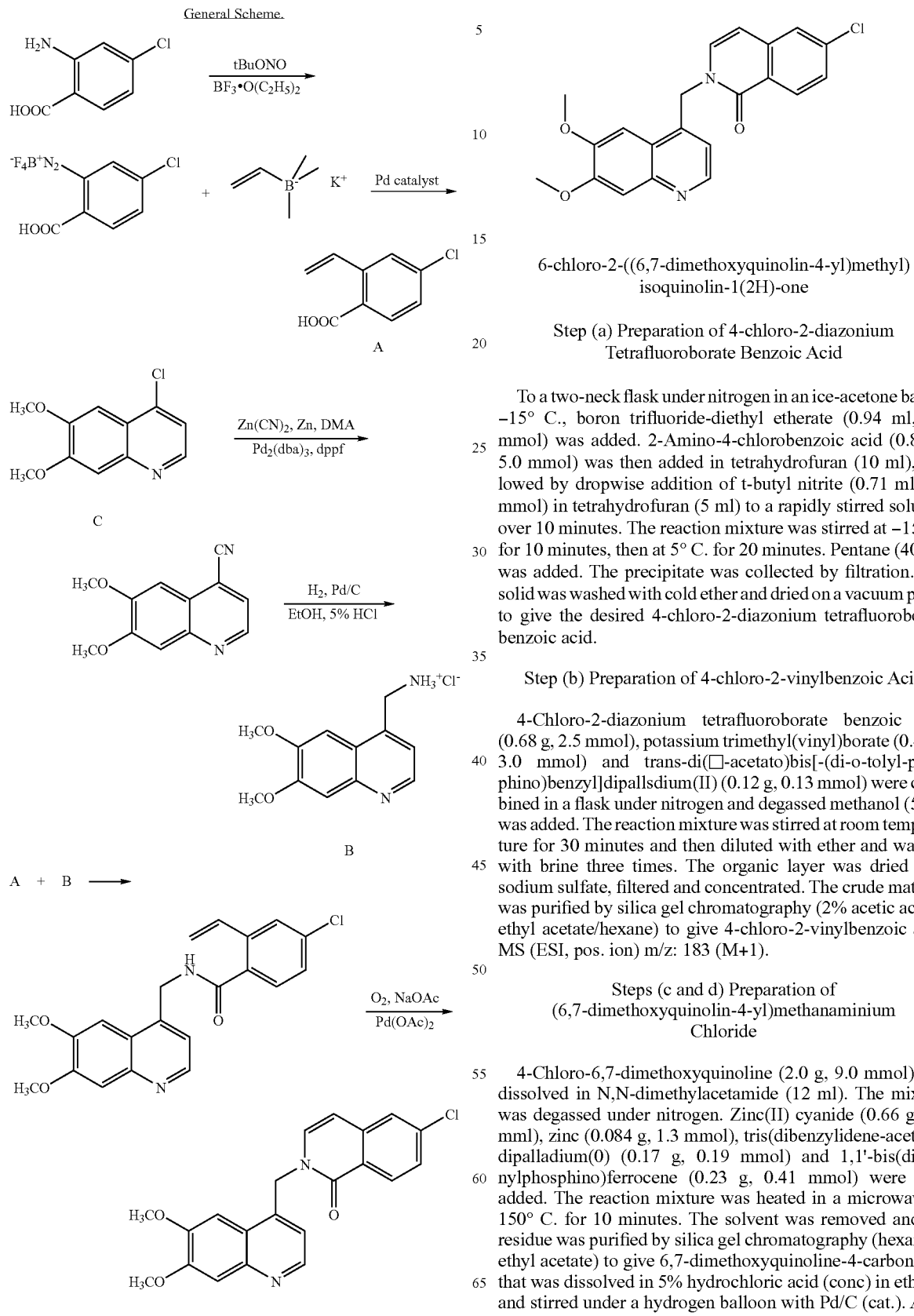

Example 11

6-chloro-2-((6,7-dimethoxyquinolin-4-yl)methyl) isoquinolin-1(2H)-one

Step (a) Preparation of 4-chloro-2-diazonium Tetrafluoroborate Benzoic Acid

To a two-neck flask under nitrogen in an ice-acetone bath at −15° C., boron trifluoride-diethyl etherate (0.94 ml, 7.5 mmol) was added. 2-Amino-4-chlorobenzoic acid (0.86 g, 5.0 mmol) was then added in tetrahydrofuran (10 ml), followed by dropwise addition of t-butyl nitrite (0.71 ml, 6.0 mmol) in tetrahydrofuran (5 ml) to a rapidly stirred solution over 10 minutes. The reaction mixture was stirred at −15° C. for 10 minutes, then at 5° C. for 20 minutes. Pentane (40 ml) was added. The precipitate was collected by filtration. The solid was washed with cold ether and dried on a vacuum pump to give the desired 4-chloro-2-diazonium tetrafluoroborate benzoic acid.

Step (b) Preparation of 4-chloro-2-vinylbenzoic Acid

4-Chloro-2-diazonium tetrafluoroborate benzoic acid (0.68 g, 2.5 mmol), potassium trimethyl(vinyl)borate (0.40 g, 3.0 mmol) and trans-di(☐-acetato)bis[-(di-o-tolyl-phosphino)benzyl]dipallsdium(II) (0.12 g, 0.13 mmol) were combined in a flask under nitrogen and degassed methanol (5 ml) was added. The reaction mixture was stirred at room temperature for 30 minutes and then diluted with ether and washed with brine three times. The organic layer was dried over sodium sulfate, filtered and concentrated. The crude material was purified by silica gel chromatography (2% acetic acid in ethyl acetate/hexane) to give 4-chloro-2-vinylbenzoic acid. MS (ESI, pos. ion) m/z: 183 (M+1).

Steps (c and d) Preparation of (6,7-dimethoxyquinolin-4-yl)methanaminium Chloride 4-Chloro-6,7-dimethoxyquinoline (2.0 g, 9.0 mmol) was dissolved in N,N-dimethylacetamide (12 ml). The mixture was degassed under nitrogen. Zinc(II) cyanide (0.66 g, 5.8 mml), zinc (0.084 g, 1.3 mmol), tris(dibenzylidene-acetone)dipalladium(0) (0.17 g, 0.19 mmol) and 1,1'-bis(diphenylphosphino)ferrocene (0.23 g, 0.41 mmol) were then added. The reaction mixture was heated in a microwave at 150° C. for 10 minutes. The solvent was removed and the residue was purified by silica gel chromatography (hexane to ethyl acetate) to give 6,7-dimethoxyquinoline-4-carbonitrile that was dissolved in 5% hydrochloric acid (conc) in ethanol and stirred under a hydrogen balloon with Pd/C (cat.). After filtration through celite, the filtrate was collected and concentrated to give (6,7-dimethoxyquinolin-4-yl)methanaminium chloride. MS (ESI, pos. ion) m/z: 219 (M+1).

Step (e) Preparation of 4-chloro-N-((6,7-dimethoxyquinolin-4-yl)methyl)-2-vinylbenzamide (6,7-Dimethoxyquinolin-4-yl)methanaminium chloride (0.80 g, 2.8 mmol), 4-chloro-2-vinylbenzoic acid (0.46 g, 2.5 mmol), N-(3-dimethylaminopropyl)-N'-ethylcarbodiimide hydrochloride (0.58 g, 3.0 mmol) and 1-hydroxybenzotriazole hydrate (0.41 g, 3.0 mmol) were combined in methylene chloride (30 ml), then triethylamine (1.4 ml, 10.0 mmol) was added. The reaction mixture was stirred at room temperature overnight. The solvent was removed and the residue was purified by silica gel chromatography (ethyl acetate) to give 4-chloro-N-((6,7-dimethoxyquinolin-4-yl)methyl)-2-vinylbenzamide. MS (ESI, pos. ion) m/z: 383 (M+1).

Step (f) Preparation of 6-chloro-2-((6,7-dimethoxyquinolin-4-yl)methyl)isoquinolin-1(2H)-one 4-Chloro-N-((6,7-dimethoxyquinolin-4-yl)methyl)-2-vinylbenzamide (0.084 g, 0.22 mmol), sodium acetate (0.036 g, 0.44 mmol), and palladium acetate (0.002 g, 0.011 mmol) were combined in DMSO (5 ml). The reaction mixture was stirred under an oxygen balloon at 100° C. overnight. The mixture was poured into water and extracted with ethyl acetate three times. The combined organic layers were washed with water and brine, dried over sodium sulfate, filtered and concentrated. The crude material was purified by prep-TLC plate with ethyl acetate to give 6-chloro-2-((6,7-dimethoxyquinolin-4-yl)methyl)isoquinolin-1(2H)-one. MS (ESI, pos. ion) m/z: 381 (M+1). $^1$H NMR (CDCl$_3$): 4.03 (6H, s), 4.80 (1H, d), 5.95 (1H, d), 5.40 (2H, s), 7.05 (1H, d), 7.40 (1H, s), 7.56 (2H, m), 7.70 (1H, s), 7.87 (1H, d), 8.64 (1H, d). Method 10.

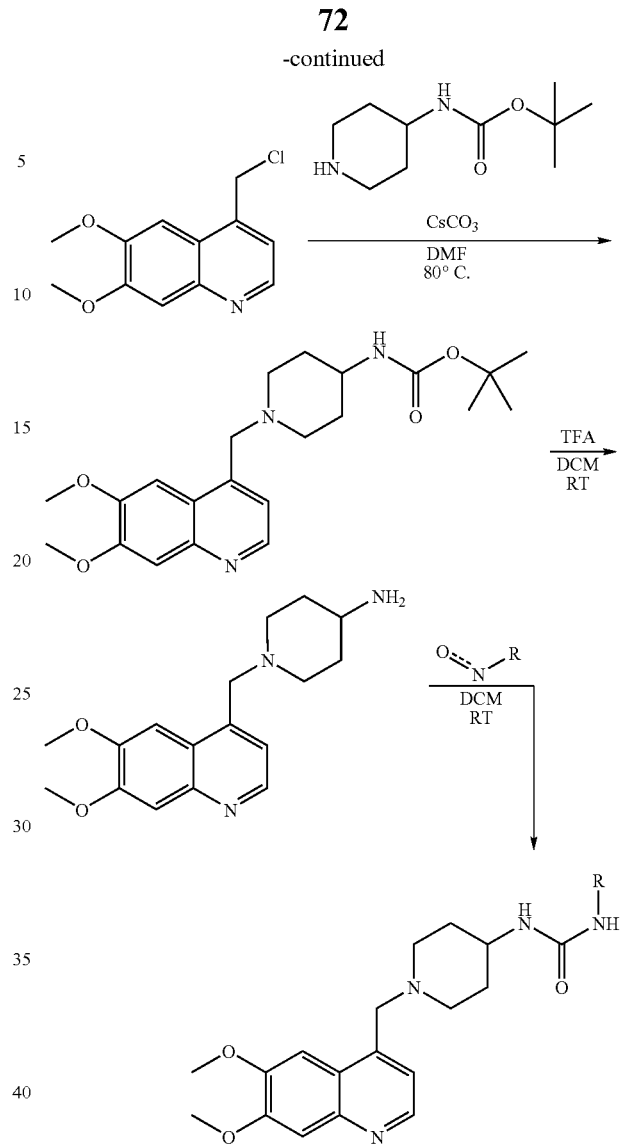

Example 12

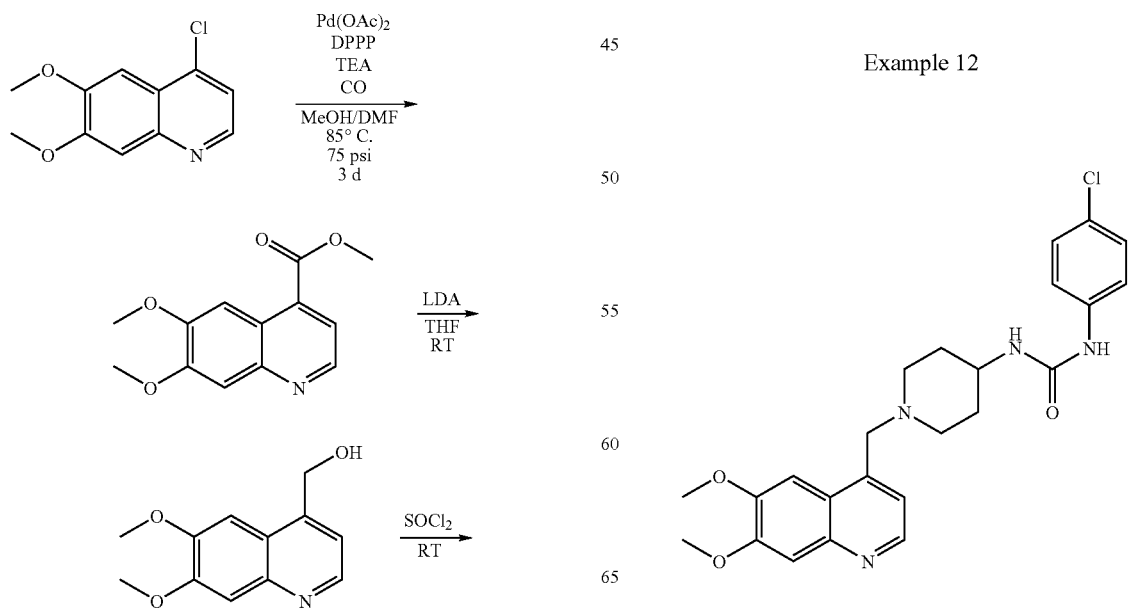

1-(4-chlorophenyl)-3-(1-((6,7-dimethoxyquinolin-4-yl)methyl)piperidin-4-yl)urea

Step (a) Preparation of 4-(chloromethyl)-6,7-dimethoxyquinoline Hydrochloride

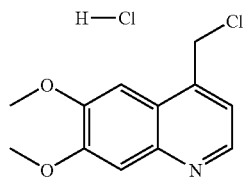

4-(Chloromethyl)-6,7-dimethoxyquinoline hydrochloride was prepared as previously described in Method 6.

Step (b) Preparation of tert-butyl 1-((6,7-dimethoxyquinolin-4-yl)methyl)piperidin-4-ylcarbamate 4-(Chloromethyl)-6,7-dimethoxyquinoline hydrochloride (0.75 g, 2.74 mmol), tert-butyl piperidin-4-ylcarbamate (0.77 g, 3.84 mmol), and cesium carbonate (2.68 g, 8.23 mmol) were dissolved in DMF (14 mL) and heated to 80° C. while stirring. After 4 hours, the reaction was cooled, DMF was removed, and the compound was taken up in DCM (150 mL) and water (20 mL). The aqueous layer was extracted 2× with DCM (50 mL). The organics were washed with brine, dried with sodium sulfate, and concentrated to give the desired product tert-butyl 1-((6,7-dimethoxyquinolin-4-yl)methyl)piperidin-4-ylcarbamate (1.04 g, 2.60 mmol, 95% yield). MS (ESI pos. ion) m/z: 402.2 (MH+). Calc'd exact mass for $C_{22}H_{31}N_3O_4$: 401. $^1$HNMR (400 MHz, CDCl$_3$): 8.64-8.65 (d, J=4.4 Hz, 1H), 7.58 (s, 1H), 7.42 (s, 1H), 7.23-7.24 (d, J=4.4 Hz, 1H), 4.57-4.59 (m, 1H), 4.03 (s, 3H), 4.01 (s, 3H), 3.83 (s, 2H), 2.82-2.85 (bd, J=11.6 Hz, 2H), 2.18-2.24 (bt, J=10.8 Hz, 2H), 1.92-1.95 (bd, J=12.4 Hz, 2H), 1.44 (s, 9H), 1.41-1.44 (m, 2H, overlapping).

Step (c) Preparation of 1-((6,7-dimethoxyquinolin-4-yl)methyl)piperidin-4-amine tert-Butyl 1-((6,7-dimethoxyquinolin-4-yl)methyl)piperidin-4-ylcarbamate (1 g, 2.49 nmol) was dissolved in DCM (25 mL). While stirring, TFA (1.9 mL, 25 mmol) was added dropwise at rt, and the reaction was allowed to stir for 15 hours. The solvent was removed and the crude compound was taken up in EtOAc (150 mL) and washed with sat. sodium bicarbonate (20 mL). The organics were washed with brine, dried with sodium sulfate, and concentrated. The mixture was columned using 100% DCM to 7% MeOH to give the desired product 1-((6,7-dimethoxyquinolin-4-yl)methyl)piperidin-4-amine (0.54 g, 1.79 mmol, 72% yield). MS (ESI pos. ion) m/z: 302.2 (MH+). Calc'd exact mass for $C_{17}H_{23}N_3O_2$: 301. $^1$HNMR (400 MHz, CDCl3): 8.63-8.64 (d, J=4.4 Hz, 1H), 7.63 (s, 1H), 7.41 (s, 1H), 7.22-7.23 (d, J=4.4 Hz, 1H), 4.03 (s, 3H), 4.01 (s, 3H), 3.83 (s, 2H), 2.84-2.87 (bd, J=12.0 Hz, 2H), 2.70-2.73 (m, 1H), 2.11-2.16 (bt, J=11.2 Hz, 2H), 1.78-1.82 (bd, J=12.8 Hz, 2 H), 1.37-1.41 (m, 2H).

Step (d) Preparation of 1-(4-chlorophenyl)-3-(1-((6,7-dimethoxyquinolin-4-yl)methyl)piperidin-4-yl)urea 1-((6,7-Dimethoxyquinolin-4-yl)methyl)piperidin-4-amine (150 mg, 0.50 mmol) was dissolved in DCM (5 mL). While stirring, 4-chlorophenyl isocyanate (84 uL, 0.65 mmol) was added dropwise at rt, and the reaction was allowed to stir for 15 hours. The solvent was removed and the crude compound was columned using 100% DCM to 5% MeOH to give the desired product 1-(4-chlorophenyl)-3-(1-((6,7-dimethoxyquinolin-4-yl)methyl)piperidin-4-yl)urea (50 mg, 0.11 mmol, 22% yield). MS (ESI pos. ion) m/z: 455.2 (MH+). Calc'd exact mass for $C_{24}H_{27}ClN_4O_3$: 454.

The following compounds were synthesized using Method 10. In each case, the appropriate isocyanate was used in the last step.

| Ex. | Structure | Method of Synthesis | MS (ESI, pos. ion) m/z (M + H) |
|---|---|---|---|
| 12A | 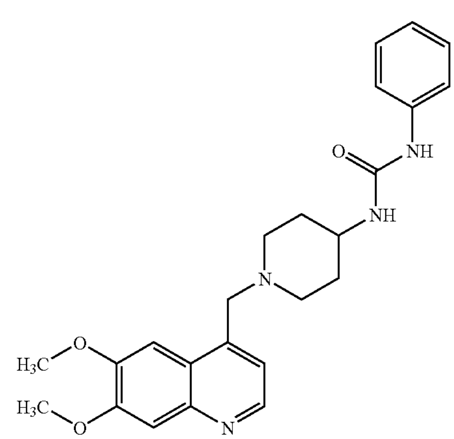 | 10 | 421.1 |

-continued

| Ex. | Structure | Method of Synthesis | MS (ESI, pos. ion) m/z (M + H) |
|---|---|---|---|
| 12B | 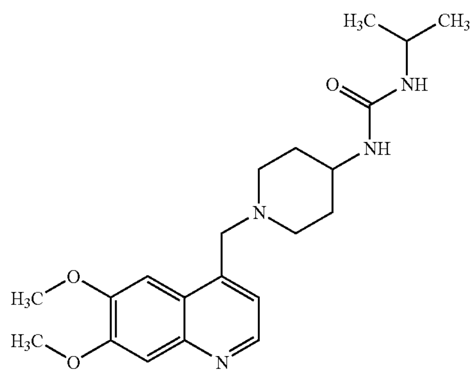 | 10 | 387.2 |
| 12C | 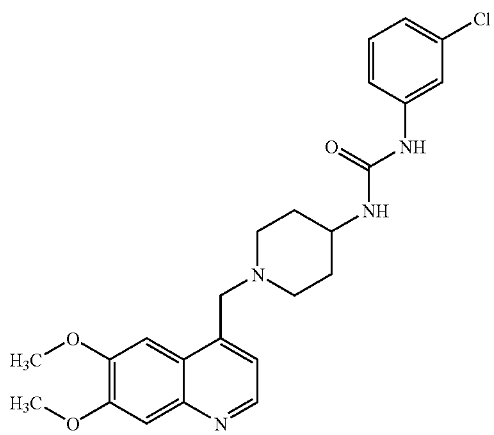 | 10 | 455.1 |
| 12D | 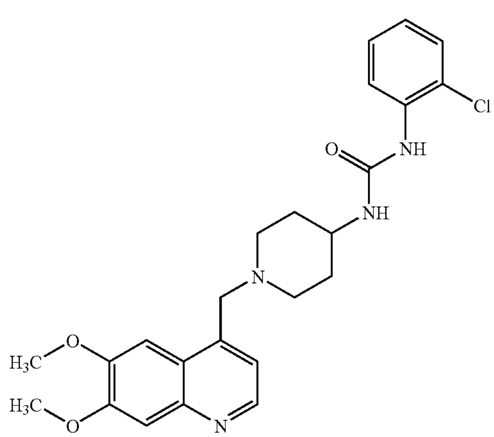 | 10 | 455.2 |

-continued
| Ex. | Structure | Method of Synthesis | MS (ESI, pos. ion) m/z (M + H) |
|---|---|---|---|
| 12E | 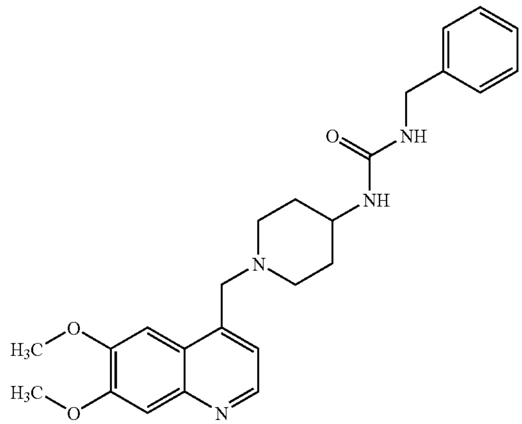 | 10 | 435.2 |
Method 11.
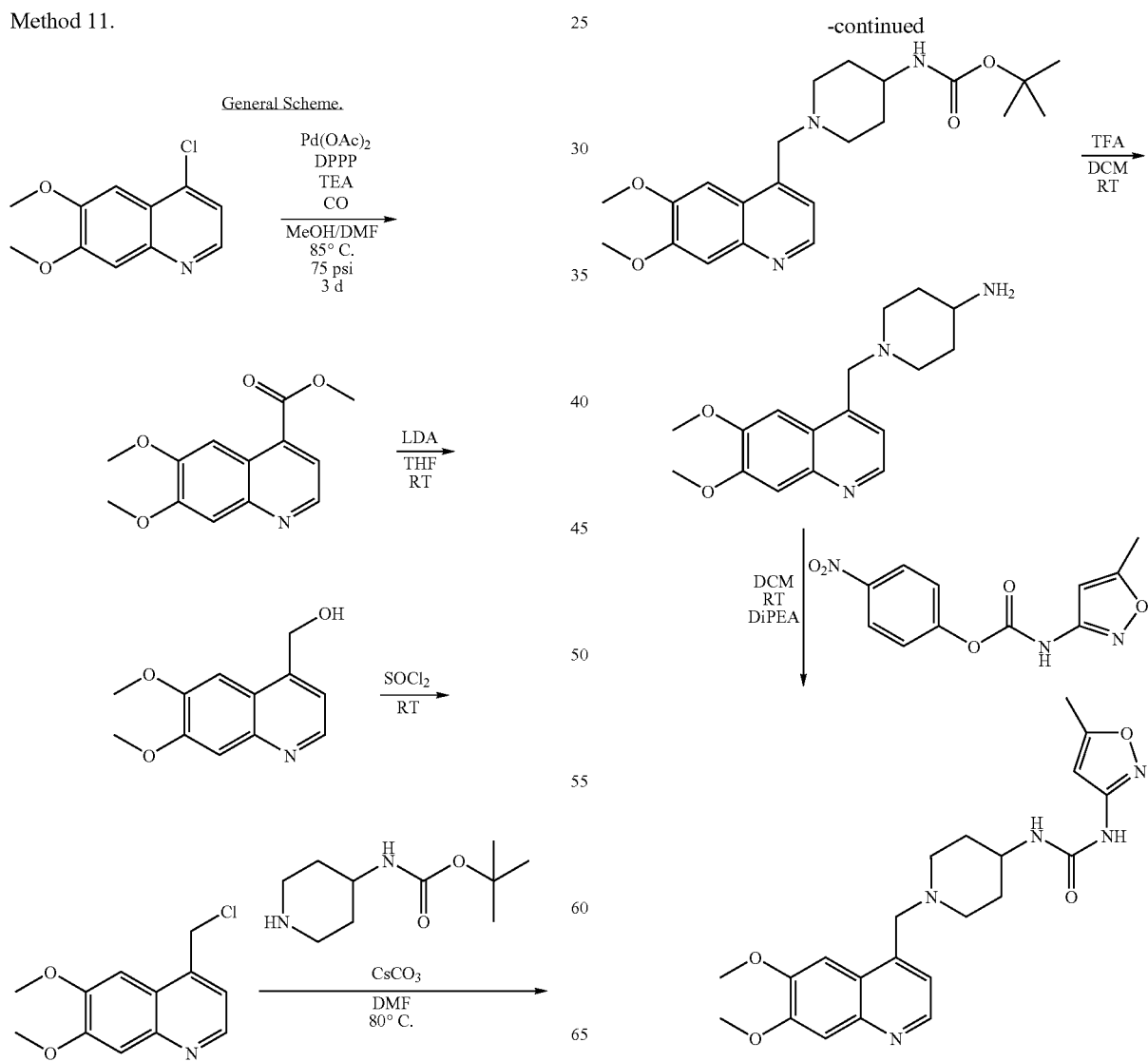

Example 13

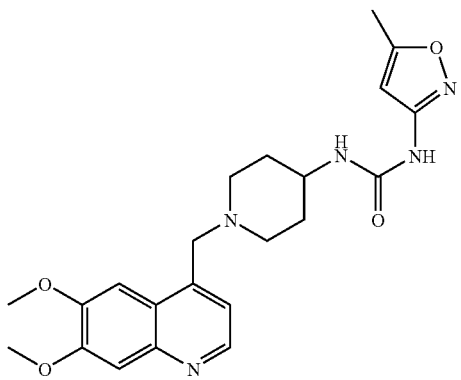

1-(1-((6,7-dimethoxyquinolin-4-yl)methyl)piperidin-4-yl)-3-(5-methylisoxazol-3-yl)urea Step (a-e) Preparation of 1-((6,7-dimethoxyquinolin-4-yl)methyl)piperidin-4-amine 1-((6,7-Dimethoxyquinolin-4-yl)methyl)piperidin-4-amine was prepared as previously described in Method 10.

Step (f) Preparation of 4-nitrophenyl thiazol-2-ylcarbamate

A solution of 5-methylisoxazol-3-amine (250 mg, 2.59 mmol) and p-nitrophenyl chloroformate (539 mg, 2.68 mmol) in THF (6 mL) was stirred for 15 minutes at RT before the solution was concentrated in vacuo. The title compound was used immediately in the following reaction without further purification. MS (ESI, pos. ion) m/z: 264.1 (M+1). Mass cal'd for $C_{11}H_9N_3O_5$: 263. ¹HNMR (400 MHz, CDCl3): 8.30-8.32 (d, J=9.2 Hz, 2H), 7.72 (bs, 1H), 7.39-7.41 (d, J=8.8 Hz, 2H), 6.54 (s, 1H), 2.41 (s, 3H).

Step (g) Preparation of 1-(1-((6,7-dimethoxyquinolin-4-yl)methyl)piperidin-4-yl)-3-(5-methylisoxazol-3-yl)urea To a stirring solution of 1-((6,7-dimethoxyquinolin-4-yl)methyl)piperidin-4-amine (150 mg, 0.50 mmol) and 4-nitrophenyl thiazol-2-ylcarbamate (144 mg, 0.55 mmol) in DCM (5 mL) was added DIPEA (173 uL, 1.00 mmol) at RT. The mixture was allowed to stir for 15 h before the solution was concentrated in vacuo. Purification by prep TLC plate using 15:1 DCM:MeOH yielded the desired compound 1-(1-((6,7-dimethoxyquinolin-4-yl)methyl)piperidin-4-yl)-3-(5-methylisoxazol-3-yl)urea (80 mg, 0.19 mmol, 38% yield). MS (ESI pos. ion) m/z: 426.2 (MH+). Calc'd exact mass for $C_{22}H_{27}N_5O_4$: 425. ¹HNMR (400 MHz, CDCl3): 8.66-8.67 (d, J=4.4 Hz, 1H), 8.36 (bs, 1H), 7.60 (s, 1H), 7.45 (s, 1H), 7.27-7.28 (m, 1H, covered by residual solvent), 5.83 (s, 1H), 4.05 (s, 6H), 3.87 (s, 2H), 3.83-3.85 (m, 1H), 2.83-2.85 (bd, J=10.0 Hz, 2H), 2.37 (s, 3H), 2.31-2.36 (bt, J=10.4 Hz, 2H overlapping), 1.99-2.02 (bd, J=11.2 Hz, 2H), 1.58-1.66 (m, 2H).

Although the pharmacological properties of the compounds of Formulas I-IV vary with structural change, in general, activity possessed by compounds of Formulas I-IV may be demonstrated in vivo. The pharmacological properties of the compounds of this invention may be confirmed by a number of pharmacological in vitro assays. The exemplified pharmacological assays which follow have been carried out with the compounds according to the invention and their salts. Compounds of the present invention showed inhibition of Lck kinase at doses less than 10 μM. Compounds of the present invention also showed inhibition of VEGFR kinase at doses less than 10 μM.

Biological Testing

The pharmacological properties of the compounds of this invention may be confirmed by in vitro assays such as those described below, as well as other methods known in the art.

HUVEC Proliferation Assay

Human Umbilical Vein Endothelial cells are purchased from Clonetics, Inc., as cryopreserved cells harvested from a pool of donors. These cells, at passage 1, are thawed and expanded in EBM-2 complete medium, until passage 2 or 3. The cells are trypsinized, washed in DMEM+10% FBS+antibiotics, and spun at 1000 rpm for 10 min. Prior to centrifugation of the cells, a small amount is collected for a cell count. After centrifugation, the medium is discarded, and the cells are resuspended in the appropriate volume of DMEM+10% FBS+antibiotics to achieve a concentration of $3 \times 10^5$ cells/mL. Another cell count is performed to confirm the cell concentration. The cells are diluted to $3 \times 10^4$ cells/mL in DMEM+10% FBS+antibiotics, and 100 μL of cells are added to a 96-well plate. The cells are incubated at 37° C. for 22 h.

Prior to the completion of the incubation period, compound dilutions are prepared. Five-point, five-fold serial dilutions are prepared in DMSO, at concentrations 400-fold greater than the final concentrations desired. 2.5 μL of each compound dilution are diluted further in a total of 1 mL DMEM+10% FBS+antibiotics (400× dilution). Medium containing 0.25% DMSO is also prepared for the 0 μM compound sample. At the 22 h timepoint, the medium is removed from the cells, and 100 μL of each compound dilution is added. The cells are incubated at 37° C. for 2-3 h.

During the compound pre-incubation period, the growth factors are diluted to the appropriate concentrations. Solutions of DMEM+10% FBS+antibiotics, containing either VEGF or bFGF at the following concentrations: 50, 10, 2, 0.4, 0.08, and 0 ng/mL are prepared. For the compound-treated cells, solutions of VEGF at 550 ng/mL or bFGF at 220 ng/mL for 50 ng/mL or 20 ng/mL final concentrations, respectively, are prepared since 10 μL of each will be added to the cells (110 μL final volume). At the appropriate time after adding the compounds, the growth factors are added. VEGF is added to one set of plates, while bFGF is added to another set of plates. For the growth factor control curves, the media on wells B4-G6 of plates 1 and 2 are replaced with media containing VEGF or bFGF at the varying concentrations (50-0 ng/mL). The cells are incubated at 37° C. for an additional 72 h.

At the completion of the 72 h incubation period, the medium is removed, and the cells are washed twice with PBS. After the second wash with PBS, the plates are tapped gently to remove excess PBS, and the cells are placed at −70° C. for at least 30 min. The cells are thawed and analyzed using the CyQuant fluorescent dye (Molecular Probes C-7026), following the manufacturer's recommendations. The plates are read on a Victor/Wallac 1420 workstation at 485 nm/530 nm (excitation/emission). Raw data are collected and analyzed using a 4-parameter fit equation in XLFit. $IC_{50}$ values are then determined.

Rat Corneal Neovascularization Micropocket Model

In Life Aspects: Female Sprague Dawley rats weighing approximately 250 g were randomized into one of five treatment groups. Pretreatment with the vehicle or compound was administered orally, 24 h prior to surgery and continued once a day for seven additional days. On the day of surgery, the rats were temporarily anesthetized in an Isofluorane gas chamber (delivering 2.5 liters/min oxygen+5% Isofluorane). An othoscope was then placed inside the mouth of the animal to visualize the vocal cords. A tip-blunted wire was advanced in between the vocal cords and used as a guide for the placement of an endotracheal Teflon tube (Small Parts Inc. TFE-standard Wall R-SWTT-18). A volume-controlled ventilator (Harvard Apparatus, Inc. Model 683) was connected to the endotracheal tube to deliver a mixture of oxygen and 3% Isofluorane. Upon achieving deep anesthesia, the whiskers were cut short and the eye areas and eyes gently washed with Betadine soap and rinsed with sterile saline. The corneas were irrigated with one to two drops of Proparacaine HCl ophthalmic topical anesthetic solution (0.5%) (Bausch and Lomb Pharmaceuticals, Tampa Fla.). The rat was then positioned under the dissecting microscope and the corneal surface brought into focus. A vertical incision was made on the midline of the cornea using a diamond blade knife. A pocket was created by using fine scissors to separate the connective tissue layers of the stroma, tunneling towards the limbus of the eye. The distance between the apex of the pocket and the limbus was approximately 1.5 mm. After the pocket had been made, the soaked nitrocellulose disk filter (Gelman Sciences, Ann Arbor Mich.) was inserted under the lip of the pocket. This surgical procedure was performed on both eyes. rHu-bFGF soaked disks were placed into the right eye, and the rHu-VEGF soaked disks were placed into the left eye. Vehicle soaked disks were placed in both eyes. The disk was pushed into position at the desired distance from the limbal vessels. Ophthalmic antibiotic ointment was applied to the eye to prevent drying and infection. After seven days, the rats were euthanized by $CO_2$ asphyxiation, and the eyes enucleated. The retinal hemisphere of the eye was windowed to facilitate fixation, and the eye placed into formalin overnight.

Post Mortem Aspects: After 24 h in fixative, the corneal region of interest was dissected out from the eye, using fine forceps and a razorblade. The retinal hemisphere was trimmed off and the lens extracted and discarded. The corneal dome was bisected and the superfluous cornea trimmed off. The iris, conjunctiva and associated limbal glands were then carefully teased away. Final cuts were made to generate a square 3×3 mm containing the disk, the limbus, and the entire zone of neovascularization.

Gross Image Recording: The corneal specimens were digitally photographed using a Sony CatsEye DKC5000 camera (A.G. Heinz, Irvine Calif.) mounted on a Nikon SMZ-U stereo microscope (A.G. Heinz). The corneas were submerged in distilled water and photographed via trans-illumination at approximately 5.0 diameters magnification.

Image analysis: Numerical endpoints were generated using digital micrographs collected from the whole mount corneas after trimming and were used for image analysis on the Metamorph image analysis system (Universal Imaging Corporation, West Chester Pa.). Three measurements were taken: Disk placement distance from the limbus, number of vessels intersecting a 2.0 mm perpendicular line at the midpoint of the disk placement distance, and percent blood vessel area of the diffusion determined by thresholding.

General Formulations:

0.1% BSA in PBS vehicle: 0.025 g of BSA was added to 25.0 mL of sterile 1× phosphate buffered saline, gently shaken until fully dissolved, and filtered at 0.2 µM. Individual 1.0 mL samples were aliquoted into 25 single-use vials, and stored at −20° C. until use. For the rHu-bFGF disks, a vial of this 0.1% BSA solution was allowed to thaw at RT. Once thawed, 10 µL of a 100 mM stock solution of DTT was added to the 1 ml BSA vial to yield a final concentration of 1 mM DTT in 0.1% BSA.

rHu-VEGF Dilutions: Prior to the disk implant surgery, 23.8 µL of the 0.1% BSA vehicle above was added to a 10 µg rHu-VEGF lyophilized vial yielding a final concentration of 10 µM.

rHu-bFGF: Stock concentration of 180 ng/µL: R&D rHu-bFGF: Added 139 µL of the appropriate vehicle above to the 25 µg vial lyophilized vial. 13.3 µL of the [180 ng/µL] stock vial and added 26.6 µL of vehicle to yield a final concentration of 3.75 µM concentration.

Nitro-cellulose disk preparation: The tip of a 20-gauge needle was cut off square and beveled with emery paper to create a punch. This tip was then used to cut out ≈0.5 mm diameter disks from a nitrocellulose filter paper sheet (Gelman Sciences). Prepared disks were then placed into Eppendorf microfuge tubes containing solutions of either 0.1% BSA in PBS vehicle, 10 µM rHu-VEGF (R&D Systems, Minneapolis, Minn.), or 3.75 µM rHu-bFGF (R&D Systems, Minneapolis, Minn.) and allowed to soak for 45-60 min before use. Each nitrocellulose filter disk absorbs approximately 0.1 µL of solution.

Tumor Model

A431 cells (ATCC) are expanded in culture, harvested and injected subcutaneously into 5-8 week old female nude mice (CD1 nu/nu, Charles River Labs) (n=5-15). Subsequent administration of compound by oral gavage (10-200 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (Ora-Plus, pH 2.0) is the negative control.

LCK-Homogeneous Time Resolved Fluorescent (HTRF) Kinase Assay:

The LCK HTRF assay begins with LCK in the presence of ATP phosphorylating the biotinylated peptide Gastrin. The reaction incubates for 90 min. To quench the assay detection reagents are added which both stop the reaction by diluting out the enzyme and chelating the metals due to the presence of EDTA. Once the detection reagents are added the assay incubates for 30 min to allow for equilibration of the detection reagents.

The LCK HTRF assay is comprised of 10 µL of compound in 100% DMSO, 15 µL of ATP and biotinylated Gastrin, and 15 µL of LCK KD GST (225-509) for a final volume of 40 µL. The final concentration of gastrin is 1.2 µM. The final concentration of ATP is 0.5 µM (Km app=0.6 µM+/−0.1) and the final concentration of LCK is 250 pM. Buffer conditions are as follows: 50 mM HEPES pH 7.5, 50 mM NaCl, 20 mM $MgCl$, 5 mM MnCl, 2 mM DTT, 0.05% BSA.

The assay is quenched and stopped with 160 µL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.0004 mg/mL, and europilated anti-phosphotyrosine Ab (Eu-anti-PY) at a final conc of 0.025 nM.

The assay plate is read in either a Discovery or a RubyStar. The eu-anti-PY is excited at 320 m and emits at 615 nm to excite the SA-APC which in turn emits at 655 nm. The ratio of SA-APC at 655 nm (excited due to close proximity to the Eu-anti-PY because of phosphorylation of the peptide) to free Eu-anti-PY at 615 nm will give substrate phosphorylation.

The compounds exemplified herein have been assayed and exhibit KDR $K_i$s in a range from 0.6 nm to 3 µm. Illustrative activity values are provided in the following table.

| Example | KDR $K_i$ (µM) |
|---------|----------------|
| 1       | 3              |
| 1A      | 0.3333         |
| 3A      | 0.1050         |
| 3C      | 0.0428         |
| 3D      | 0.0049         |
| 3G      | 0.0022         |
| 3H      | 0.0054         |
| 5A      | 0.0723         |
| 5C      | 0.0701         |
| 7A      | 0.0111         |
| 8C      | 0.0552         |
| 8F      | 0.0006         |
| 8H      | 0.0076         |
| 10A     | 0.0016         |
| 11      | 0.529          |

Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990, 141, WO 00/12089 and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., US Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., US Publication No. 2002/0042368), specifically binding anti-eph receptor and/or anti-ephrin antibodies or antigen binding regions (U.S. Pat. Nos. 5,981,245; 5,728,813; 5,969, 110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sima, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Formulations

Also embraced within this invention is a class of pharmaceutical compositions comprising the active compounds of Formula I-IV in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 100 mg/kg, or between about 0.01 and about 20 mg/kg, or between about 0.01 and about 10 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, EtOH, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

No unacceptable toxological effects are expected when compounds of the present invention are administered in accordance with the present invention.

All mentioned references, patents, applications and publications, are hereby incorporated by reference in their entirety, as if here written.

What is claimed is:

1. A compound of formula I

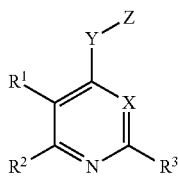

or a salt thereof wherein
X is CH;
Y is $(C_1-C_6)$alkylene, or $(C_1-C_6)$alkenylene wherein substituents on the same carbon atom or on adjacent carbon atoms may optionally combine to form a $C_3$ to $C_6$-membered cycloalkyl ring, or a $C_5-C_6$ heterocyclyl ring;
Z is

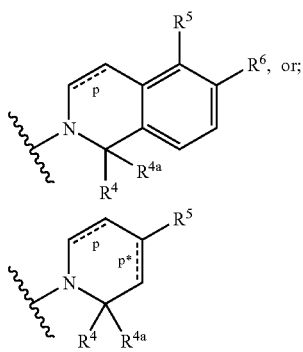

p and p* are each independently absent or a bond;
$R^1$ and $R^2$ together with the ring to which they are bonded combine to form quinoline, optionally independently substituted with one or more $R^{10}$;
$R^3$ is H, $NHR^7$, $C(=O)NHR^7$, $NHC(=O)NR^8R^9$, or $NHC(=S)NR^8R^9$;
$R^4$ and $R^{4a}$ are independently selected from H, and alkyl, or $R^4$ and $R^{4a}$ combine to form =O;
$R^5$ is H, $C(=O)NHR^7$, $NHC(=O)NHR^7$ or $NHC(=O)R^7$;
$R^6$ is H, halo, $C(=O)NHR^7$, $NHC(=O)R^7$, or $NHC(=O)NR^8R^9$;
$R^7$ is independently at each occurrence
  a) H, or
  b) alkyl, cycloalkyl, heterocyclo, aryl, heteroaryl, cycloalkyl, alkyl, arylalkyl, alkoxyalkyl, heteroarylalkyl, cycloalklyalkyl, or 2,3-dihydroindole, any of which can be optionally substituted with one or more $R^{10}$;

$R^{10}$ is halo, alkyl, alkenyl, alkynyl, alkoxy, haloalkyl, cycloalkyl, heterocyclo, aryl, heteroaryl, arylalkyl, heteroarylalkyl, cycloalkylalkyl, heterocycloalkyl, cyano, nitro, $-NR^8R^9$, $-C(=O)NR^8R^9$, or $NHC(=O)NR^8R^9$;
$R^8$ and $R^9$ are independently H, alkyl, haloalkyl, cycloalkyl, heterocyclo, aryl, heteroaryl, arylalkyl, heteroarylalkyl, cycloalkylalkyl, or heterocycloalkyl, any of which may be optionally independently substituted with one or more $R^{10}$
provided $R^5$ is not H, $C(=O)NHR^7$, or $NHC(=O)R^7$ when Z is piperidinyl.

2. A compound of claim 1 wherein Z is

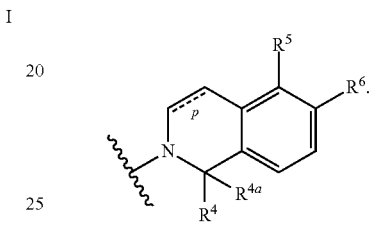

3. A compound of claim 1 wherein Z is

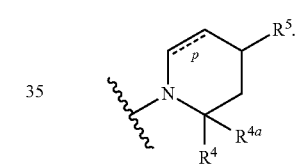

4. A compound of claim 2 wherein p is a bond.

5. A compound of claim 2 wherein p is absent.

6. A compound of claim 1 wherein Y is $CH_2$.

7. A compound of claim 5 wherein $R^1$ and $R^2$ together with the ring to which they are bonded combine to form a ring selected from 6,7-dimethoxyquinoline, and quinoline.

8. A compound of claim 7 wherein Y is $CH_2$; and $R^5$ is $C(=O)NHR^7$, $NHC(=O)R^7$ or $NHC(=O)NHR^7$.

9. A compound of claim 8 wherein $R^7$ is independently phenyl, cycloalkyl or 2,3-dihydroindole, any of which may be optionally independently substituted with one or more $R^{10}$.

10. A compound of claim 1 selected from

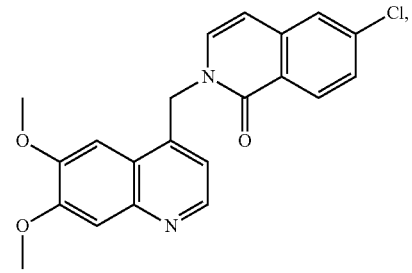

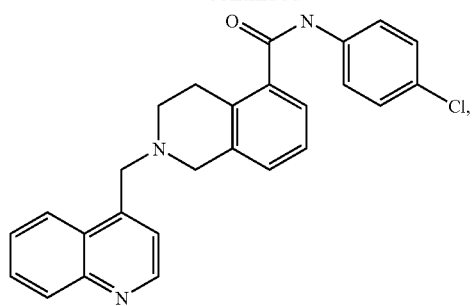
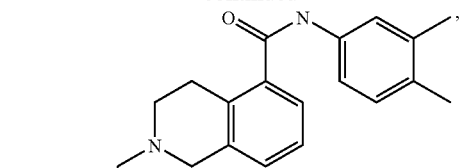
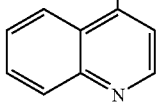
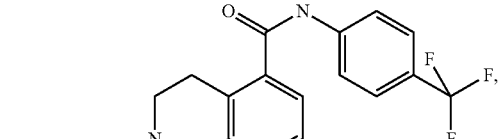
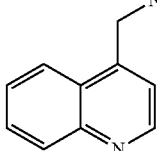
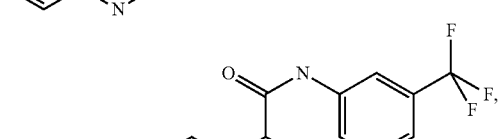
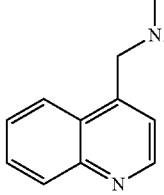
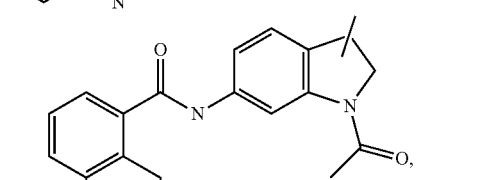
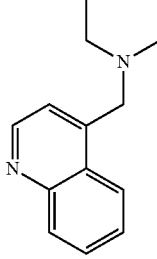
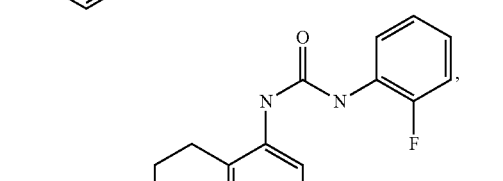
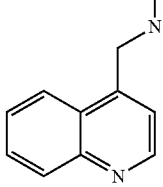

93
-continued
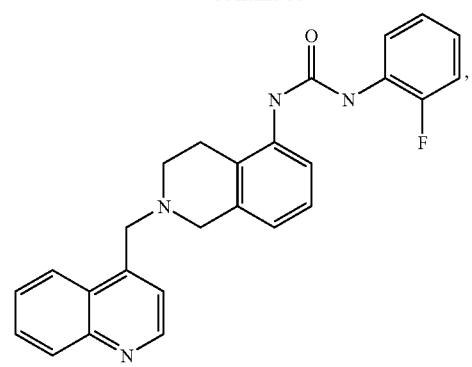
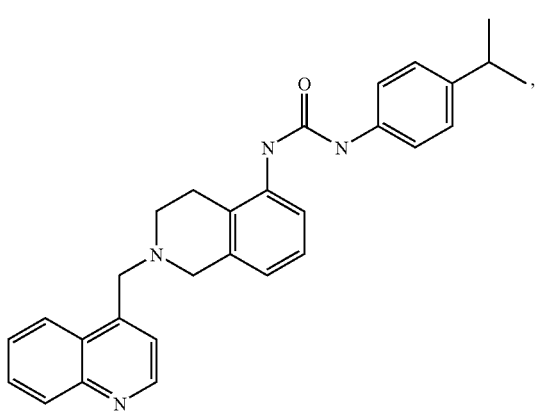
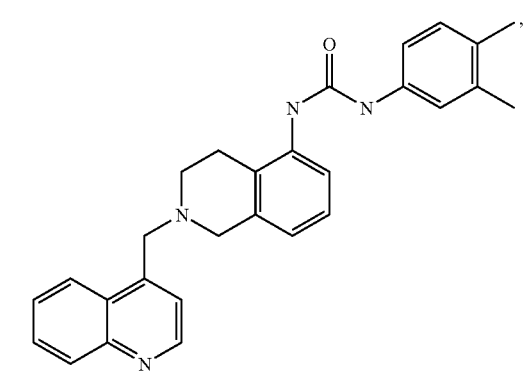
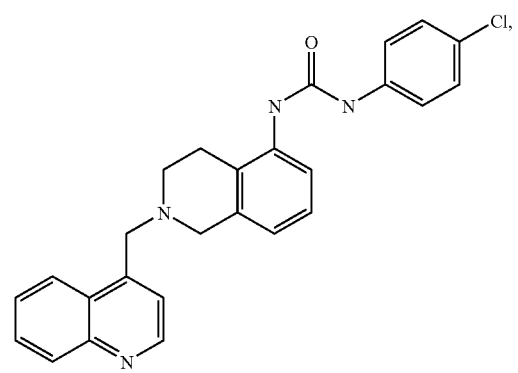
94
-continued
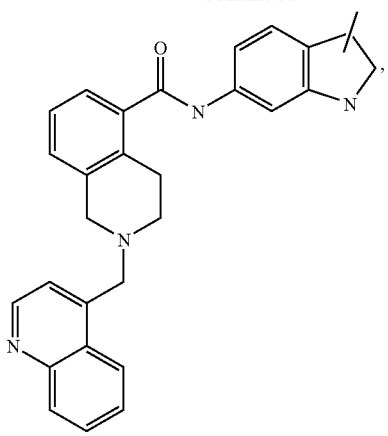
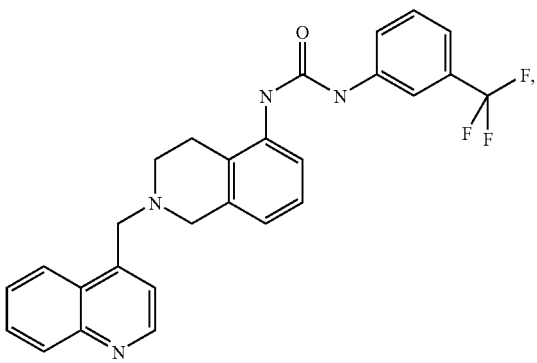
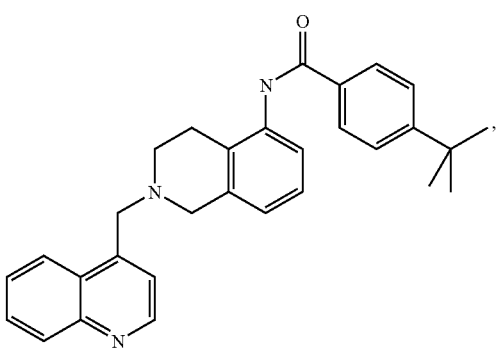
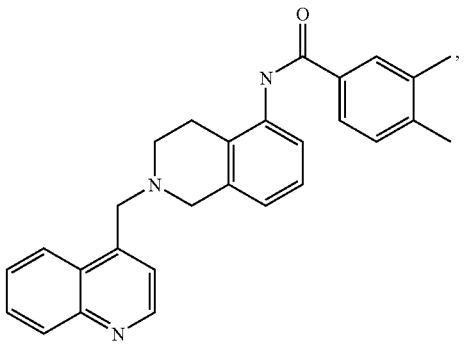

95
-continued

96
-continued

97
-continued
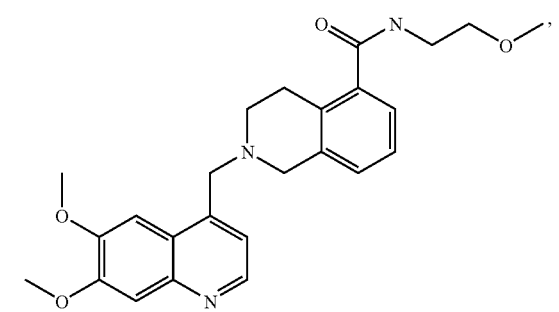
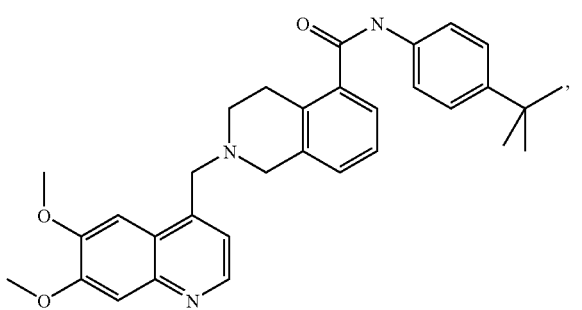
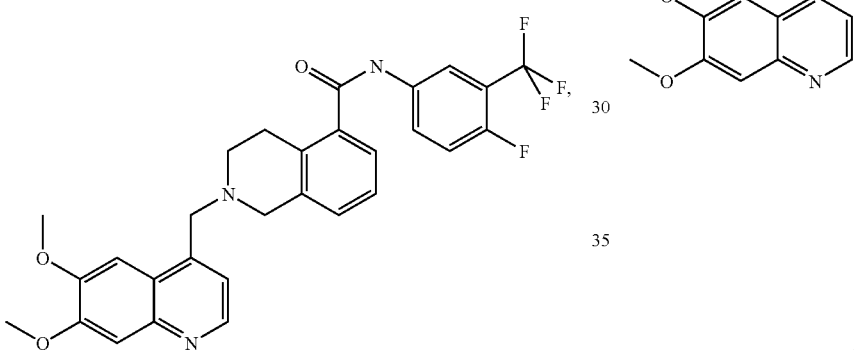
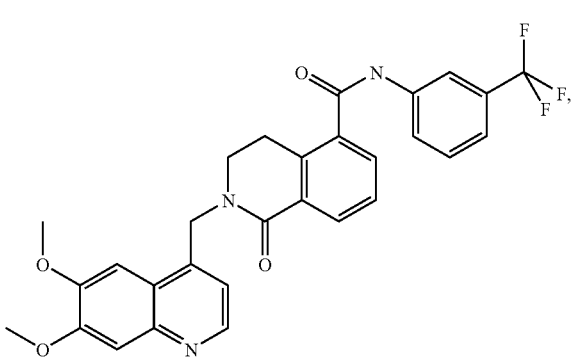
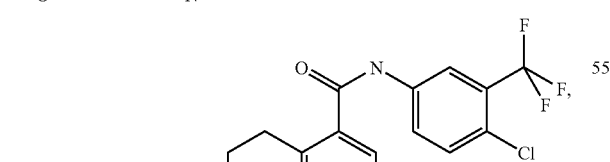
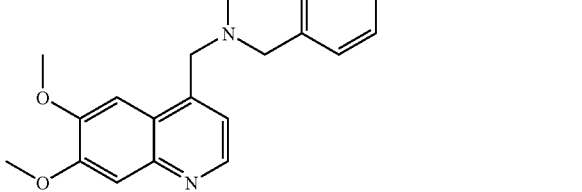
98
-continued
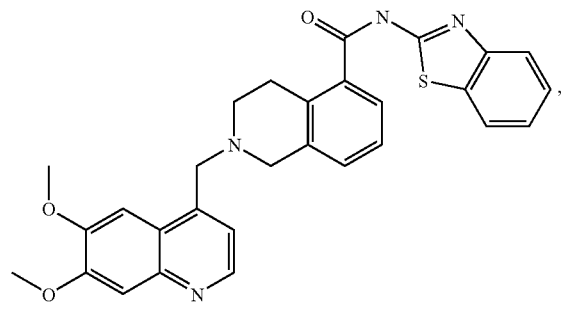
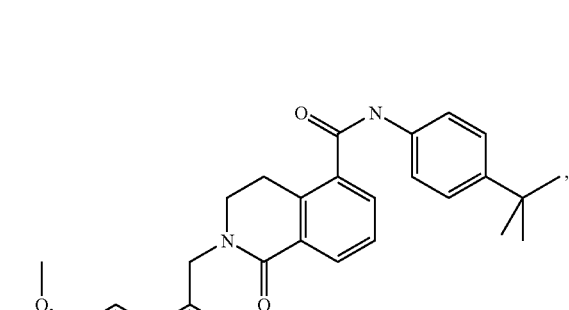
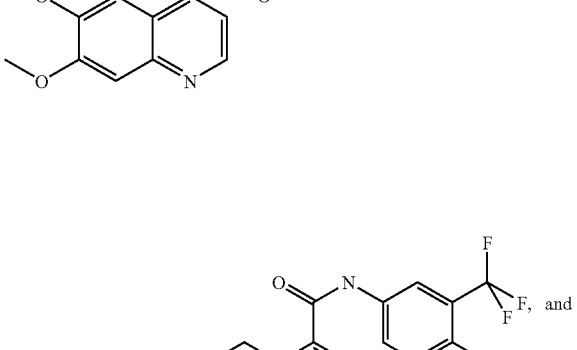
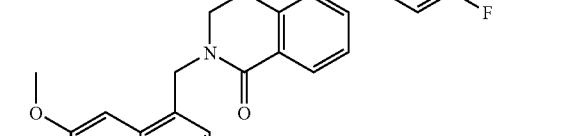
, and
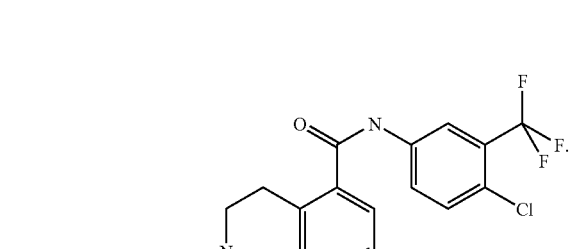
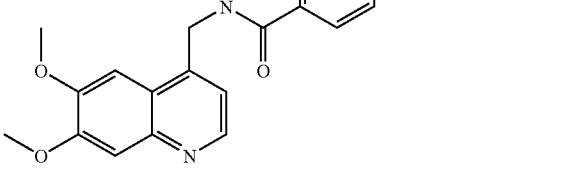

11. A compound of claim 1 selected from
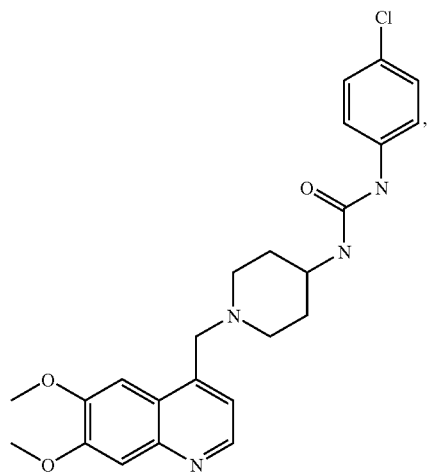
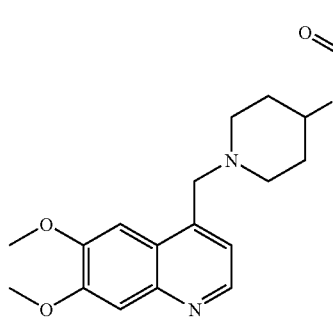
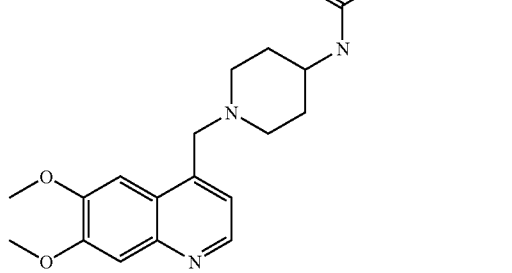
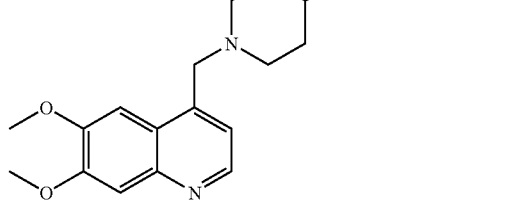
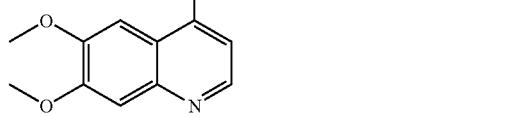

12. A compound of formula II

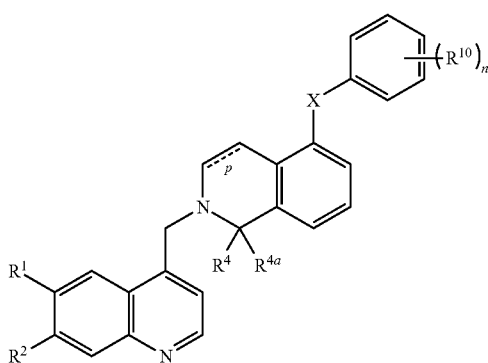

or a salt thereof wherein
$R^1$ and $R^2$ are independently H or alkoxy;
$R^4$ and $R^{4a}$ are each hydrogen, or $R^4$ and $R^{4a}$ combine to form =O;
p is absent or a bond;
X is —C(=O)NH—, —NHC(=O)NH— or —NHC(=O)—;
$R^{10}$ is independently selected at each occurrence from halo, alkyl, alkenyl, alkynyl, alkoxy, haloalkyl, cycloalkyl, heterocyclo, aryl, heteroaryl, arylalkyl, heteroarylalkyl, cycloalkylalkyl, heterocycloalkyl, cyano, nitro, —$NR^8R^9$ or —C(=O)$NR^8R^9$;
$R^8$ and $R^9$ are independently H, alkyl, haloalkyl, cycloalkyl, heterocyclo, aryl, heteroaryl, arylalkyl, heteroarylalkyl, cycloalkylalkyl, and heterocycloalkyl, any of which may be optionally independently substituted with one or more $R^{10}$; and
n is 0, 1, 2 or 3.

13. A compound of claim 12 wherein $R^1$ and $R^2$ are independently H or $C_{1-6}$ alkoxy; $R^4$ and $R^{4a}$ are each hydrogen, or $R^4$ and $R^{4a}$ combine to form =O; p is absent or a bond; X is —C(=O)NH—, —NHC(=O)NH— or —NHC(=O)—; $R^{10}$ is independently selected at each occurrence from halo, $C_{1-6}$ alkyl, $C_{2-6}$ alkenyl, $C_{2-6}$ alkynyl, $C_{1-6}$ alkoxy, $C_{1-6}$ haloalkyl, $C_{3-6}$ cycloalkyl, 3- to 6-membered heterocyclo, phenyl, naphthyl, indenyl, tetrahydronaphthyl, indanyl, 5- to 6-membered heteroaryl, aryl-$C_{1-6}$-alkyl, $C_{5-6}$ cycloalkyl-$C_{1-6}$-alkyl, 5- or 6-membered heteroaryl-$C_{1-6}$-alkyl, cyano, nitro, —$NR^8R^9$ or —C(=O)$NR^8R^9$, $R^8$ and $R^9$ are independently H, $C_{1-6}$ alkyl, $C_{1-6}$ haloalkyl, $C_{3-6}$ cycloalkyl, 3- to 6-membered heterocyclo, phenyl, naphthyl, indenyl, tetrahydronaphthyl, indanyl, 5 to 6 membered heteroaryl, aryl-$C_{1-6}$-alkyl, heteroaryl-$C_{1-6}$-alkyl, $C_{5-6}$ cycloalkyl-$C_{1-6}$-alkyl, and 5- or 6-membered heteroaryl-$C_{1-6}$-alkyl; and n is 0, 1, or 2; or a salt thereof.

14. A compound of claim 12 wherein $R^1$ and $R^2$ are independently H or $C_{1-3}$ alkoxy; $R^4$ and $R^{4a}$ are each hydrogen, or $R^4$ and $R^{4a}$ combine to form =O; p is absent or a bond; X is —C(=O)NH—, —NHC(=O)NH— or —NHC(=O)—; $R^{10}$ is independently selected at each occurrence from halo, $C_{1-2}$ alkyl, $C_{2-4}$ alkenyl, $C_{2-4}$ alkynyl, $C_{1-3}$ alkoxy, $C_{1-2}$ haloalkyl, cyclopentyl, cyclopropyl, cyclohexyl, 3- to 6-membered heterocyclo, phenyl, 5- or 6-membered heteroaryl, benzyl, diphenylmethyl, phenylethyl, $C_{5-6}$ cycloalkyl—$C_{1-3}$-alkyl, 5- or 6-membered heteroaryl-$C_{1-3}$-alkyl, cyano, nitro, —$NR^8R^9$ or —C(=O)$NR^8R^9$, $R^8$ and $R^9$ are independently H, $C_{1-2}$ alkyl, $C_{1-2}$ haloalkyl, cyclopentyl, cyclopropyl, cyclohexyl, 3- to 6-membered heterocyclo, phenyl, heteroaryl, benzyl, diphenylmethyl, phenylethyl, $C_{5-6}$ cycloalkyl-$C_{1-3}$-alkyl, and 5- or 6-membered heteroaryl-$C_{1-6}$-alkyl; and n is 0, 1, or 2; or a salt thereof.

15. A compound of claim 3 wherein p is absent.

16. A pharmaceutical composition comprising a pharmaceutically-acceptable carrier and a compound of claim 1.

17. A pharmaceutical composition comprising a pharmaceutically-acceptable carrier and a compound of claim 12.

* * * * *